(12) United States Patent
Gharibian

(10) Patent No.: US 9,480,391 B2
(45) Date of Patent: Nov. 1, 2016

(54) PLIABLE CAMERA COVER

(71) Applicant: Noel Gharibian, Glendale, CA (US)

(72) Inventor: Noel Gharibian, Glendale, CA (US)

( * ) Notice: Subject to any disclaimer, the term of this patent is extended or adjusted under 35 U.S.C. 154(b) by 0 days.

(21) Appl. No.: 15/050,350

(22) Filed: Feb. 22, 2016

(65) Prior Publication Data

US 2016/0242630 A1   Aug. 25, 2016

Related U.S. Application Data

(60) Provisional application No. 62/119,708, filed on Feb. 23, 2015.

(51) Int. Cl.
| | | |
|---|---|---|
| G03B 17/56 | (2006.01) |
| G02B 27/00 | (2006.01) |
| A61B 1/00 | (2006.01) |

(52) U.S. Cl.
CPC ....... *A61B 1/00142* (2013.01); *G02B 27/0006* (2013.01); *G03B 17/566* (2013.01); *G03B 17/568* (2013.01)

(58) Field of Classification Search
CPC .......... A61B 1/00142; G02B 27/0006; G03B 17/566; G03B 17/568; G03B 17/08
See application file for complete search history.

(56) References Cited

U.S. PATENT DOCUMENTS

| | | | |
|---|---|---|---|
| 4,605,124 A | 8/1986 | Sandel et al. | |
| 4,844,252 A | 7/1989 | Barron et al. | |
| 4,878,156 A | 10/1989 | Hallings et al. | |
| 4,974,288 A | 12/1990 | Reasner | |
| 4,976,299 A | 12/1990 | Bickelman | |
| 5,036,446 A | 7/1991 | Quintanilla et al. | |
| 5,065,296 A | 11/1991 | Cude et al. | |
| 5,156,456 A * | 10/1992 | Hoftman | F21V 21/403 150/155 |
| 5,429,142 A | 7/1995 | Szabo et al. | |
| 5,498,230 A | 3/1996 | Adair | |
| 5,576,781 A | 11/1996 | Deleeuw | |
| 5,697,123 A | 12/1997 | Gharibitan et al. | |
| 5,709,465 A | 1/1998 | Lanzone | |
| 5,772,316 A | 6/1998 | Hoftman et al. | |
| 5,803,905 A * | 9/1998 | Allred | A61B 46/10 362/804 |
| 5,971,916 A * | 10/1999 | Koren | A61B 46/10 359/510 |
| 6,276,551 B1 | 8/2001 | Miller, II | |
| 6,346,073 B1 | 2/2002 | Thompson | |
| 6,633,328 B1 | 10/2003 | Byrd et al. | |
| 6,692,141 B2 * | 2/2004 | Jesurun | F21V 21/403 362/399 |
| 6,715,904 B2 | 4/2004 | Naughton | |
| 6,909,465 B2 * | 6/2005 | Liang | H04N 3/1575 348/143 |
| 8,052,339 B2 * | 11/2011 | Gharibian | A61B 1/00128 396/448 |
| 8,781,312 B1 * | 7/2014 | deSouza, Jr. | A45C 11/38 396/27 |
| 2008/0139881 A1 | 6/2008 | Cover et al. | |

OTHER PUBLICATIONS

Advanced Medical Designs, Inc. Light Handle Covers and Camera Handle Covers. http://www.advancemedicaldesigns.com/.

* cited by examiner

*Primary Examiner* — W B Perkey
(74) *Attorney, Agent, or Firm* — Patent Law Agency, LLC; Peter Ganjian

(57) ABSTRACT

The present invention discloses a replacement cover assembly that is comprised of a universal adapter interface unit and a soft, pliable, disposable, universal camera cover detachably coupled with the universal adapter interface unit.

23 Claims, 33 Drawing Sheets

PLIABLE CAMERA COVER

CROSS-REFERENCE TO RELATED APPLICATIONS

This Application claims the benefit of priority of co-pending U.S. Utility Provisional Patent Application No. 62/119,708, filed 23 Feb. 2015, the entire disclosure of which is expressly incorporated by reference in its entirety herein.

It should be noted that throughout the disclosure, where a definition or use of a term in any incorporated document(s) is inconsistent or contrary to the definition of that term provided herein, the definition of that term provided herein applies and the definition of that term in the incorporated document(s) does not apply.

BACKGROUND OF THE INVENTION

1. Field of the Invention

One or more embodiments of the present invention relate to camera covers, and more specifically, to universal and disposable sterile replacement camera covers that may be used in sterile environments such as an operating room that is also pliable.

2. Description of Related Art

Conventional, rigid, universal and disposable sterile replacement camera covers that may be used in sterile environments such as an operating room are well known and have been in use for a number of years, a non-limiting example of which is disclosed in U.S. Pat. No. 8,052,339 to Noel Gharibian, the entire disclosures of which is expressly incorporated by reference in its entirety herein.

Regrettably, universal camera cover types disclosed in U.S. Pat. No. 8,052,339 are rigid, weigh more, and due to their rigidity, cannot be collapsed into a compact form for a smaller and therefore, more efficient packaging. Small packaging with lighter weight is important to lower costs for delivery and also, for a more efficient storage (where there is limited storage space in a surgical room).

Further, known soft camera covers are all uniquely and specifically manufactured for replacement of a specifically corresponding Original Equipment Manufacturer (OEM) camera cover. In other words, use of a known soft cover to replace a specific camera cover for which the known soft cover was not intended would create issues with respect to the known cover being too short or too long for the camera, have tight or loose fit, or lens viewing area of the soft cover may not align properly with viewing axis of the camera lens, etc.

Regrettably, the manner of mounting known soft covers onto a camera vary widely and are end-user dependent (even for the same exact cover). For example, a user may incorrectly mount and finally position a known soft cover onto a camera without knowing that the soft cover is improperly mounted. A disadvantage would be that at best, the distance between the viewing area of known soft covers and that of camera lens would vary widely, which would provide inconsistent focusing quality of camera (assuming the cover viewing area and camera lens are still aligned). At worst, the soft cover may simply slip off of the camera during surgery due to improper mounting.

Additionally, given that known soft covers are all uniquely and specifically manufactured for replacement of a specifically corresponding OEM camera cover, their method of use and application is also varied and different for each OEM camera type, make, and model. A disadvantage of having a variety of proprietary soft covers is that an end-user must always be cognizant of correct use and application for the specific type of soft cover used for proper mounting. Further, most known soft covers are comprised of multiple pieces, making them too complicated and costly to manufacture, especially for a disposable item.

Accordingly, in light of the current state of the relevant art and the drawbacks to current soft camera covers, a need exists for a soft, pliable, sterile replacement camera cover that is disposable, universal and sterile and may be properly used with different types of cameras.

BRIEF SUMMARY OF THE INVENTION

A non-limiting, exemplary aspect of an embodiment of the present invention provides a replacement cover assembly, comprising:
  a universal adapter interface unit; and
  a soft, pliable, disposable universal replacement camera cover.

Another non-limiting, exemplary aspect of an embodiment of the present invention provides a replacement cover assembly, comprising:
  a universal adapter interface unit; and
  a soft, pliable, disposable, universal replacement camera cover detachably coupled with the universal adapter interface unit.

Still another non-limiting, exemplary aspect of an embodiment of the present invention provides A replacement cover assembly, comprising:
  a universal adapter interface unit that includes a coupling index; and
  a soft, pliable, disposable, universal replacement camera cover that detachably interlocks with the universal adapter interface unit at the coupling index.

These and other features and aspects of the invention will be apparent to those skilled in the art from the following detailed description of preferred non-limiting exemplary embodiments, taken together with the drawings and the claims that follow.

BRIEF DESCRIPTION OF THE DRAWINGS

It is to be understood that the drawings are to be used for the purposes of exemplary illustration only and not as a definition of the limits of the invention. Throughout the disclosure, the word "exemplary" may be used to mean "serving as an example, instance, or illustration," but the absence of the term "exemplary" does not denote a limiting embodiment. Any embodiment described as "exemplary" is not necessarily to be construed as preferred or advantageous over other embodiments. In the drawings, like reference character(s) present corresponding part(s) throughout.

DETAILED DESCRIPTION OF THE INVENTION

Figure 1A:
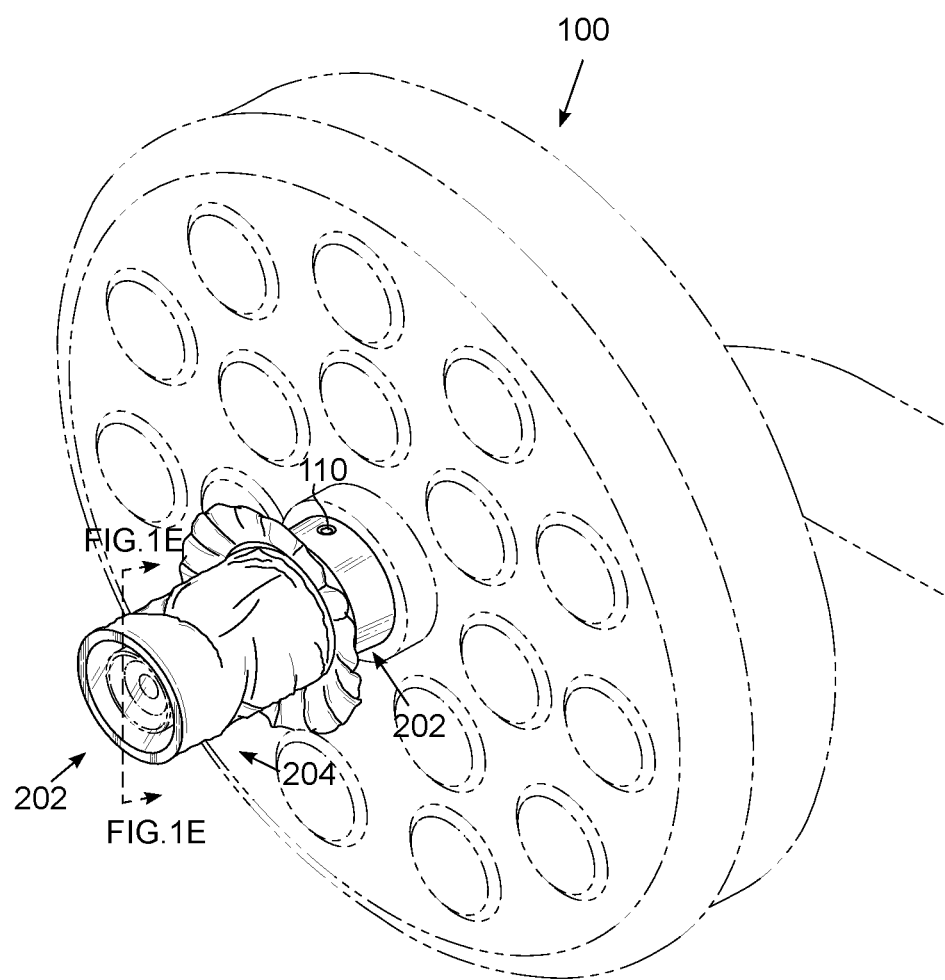
FIGS. 1A and 1B are non-limiting, exemplary perspective view illustrations of a fully assembled replacement cover assembly in accordance with one or more embodiments of the present invention, with FIGS. 1C and 1D an exploded views of the same and FIG. 1E a non-limiting, exemplary illustration of a partially cut, sectional view of the fully assembled replacement cover assembly shown in FIG. 1A.

The detailed description set forth below in connection with the appended drawings is intended as a description of presently preferred embodiments of the invention and is not intended to represent the only forms in which the present invention may be constructed and or utilized.

It is to be appreciated that certain features of the invention, which are, for clarity, described in the context of separate embodiments, may also be provided in combination in a single embodiment. Conversely, various features of the invention that are, for brevity, described in the context of a single embodiment may also be provided separately or in any suitable sub-combination or as suitable in any other described embodiment of the invention. Stated otherwise, although the invention is described below in terms of various exemplary embodiments and implementations, it should be understood that the various features and aspects described in one or more of the individual embodiments are not limited in their applicability to the particular embodiment with which they are described, but instead can be applied, alone or in various combinations, to one or more of the other embodiments of the invention.

One or more embodiments of the present invention provide a soft, pliable, sterile replacement camera cover that is disposable and universal that may generally be used with most types of cameras.

The soft, pliable, disposable, universal replacement camera cover in accordance with one or more embodiments of the present invention may be collapsed into a compact form for a smaller and therefore, more efficient packaging, which has a lighter weight and smaller form to lower costs of delivery and also, for a more efficient storage (where there is limited storage space in a surgical room).

The soft, pliable, disposable, universal replacement camera cover in accordance with one or more embodiments of the present invention may be used to replace most specific (proprietary) OEM camera covers without issues with respect to proper fit, size, viewing area alignments (between viewing area of camera lens and cover), etc.

Additionally, since the soft, pliable, sterile replacement camera cover is disposable and universal in accordance with one or more embodiments of the present invention, its method of use and application is also universal and therefore, obviating the disadvantageous requirement that an end-user must always be cognizant of correct use and application for the specific type of cover used for proper mounting.

One or more embodiments of the present invention provide a universal adapter interface unit that enables mounting of the soft, pliable, disposable, universal replacement camera cover, with the universal adapter interface unit providing an indication (e.g., an indexing feature) to end-users that the cover has mounted at a proper engagement position in accordance with one or more embodiments of the present invention. In other words, manner of mounting the soft, pliable, disposable, universal replacement camera cover is universally consistent, obviating potential improper mounting that may lead to varying distances between the viewing area of the cover and that of camera lens, which would provide inconsistent focusing quality of camera (assuming the cover viewing area and camera lens are still aligned). Further, one or more embodiments of the soft, pliable, disposable, universal replacement camera cover also obviate issues with potential slip-off from the camera during surgery due to improper installation.

Figure 1B:
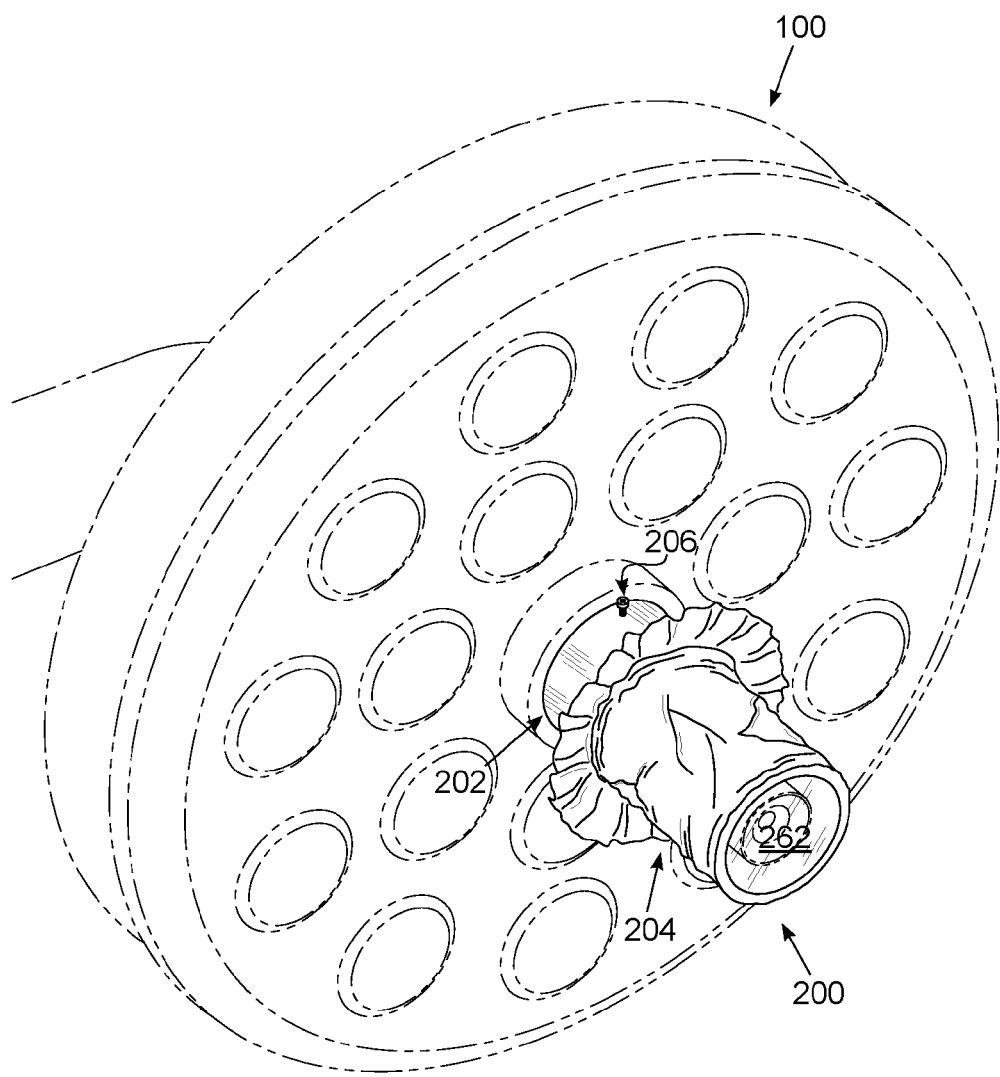
Figure 1C:
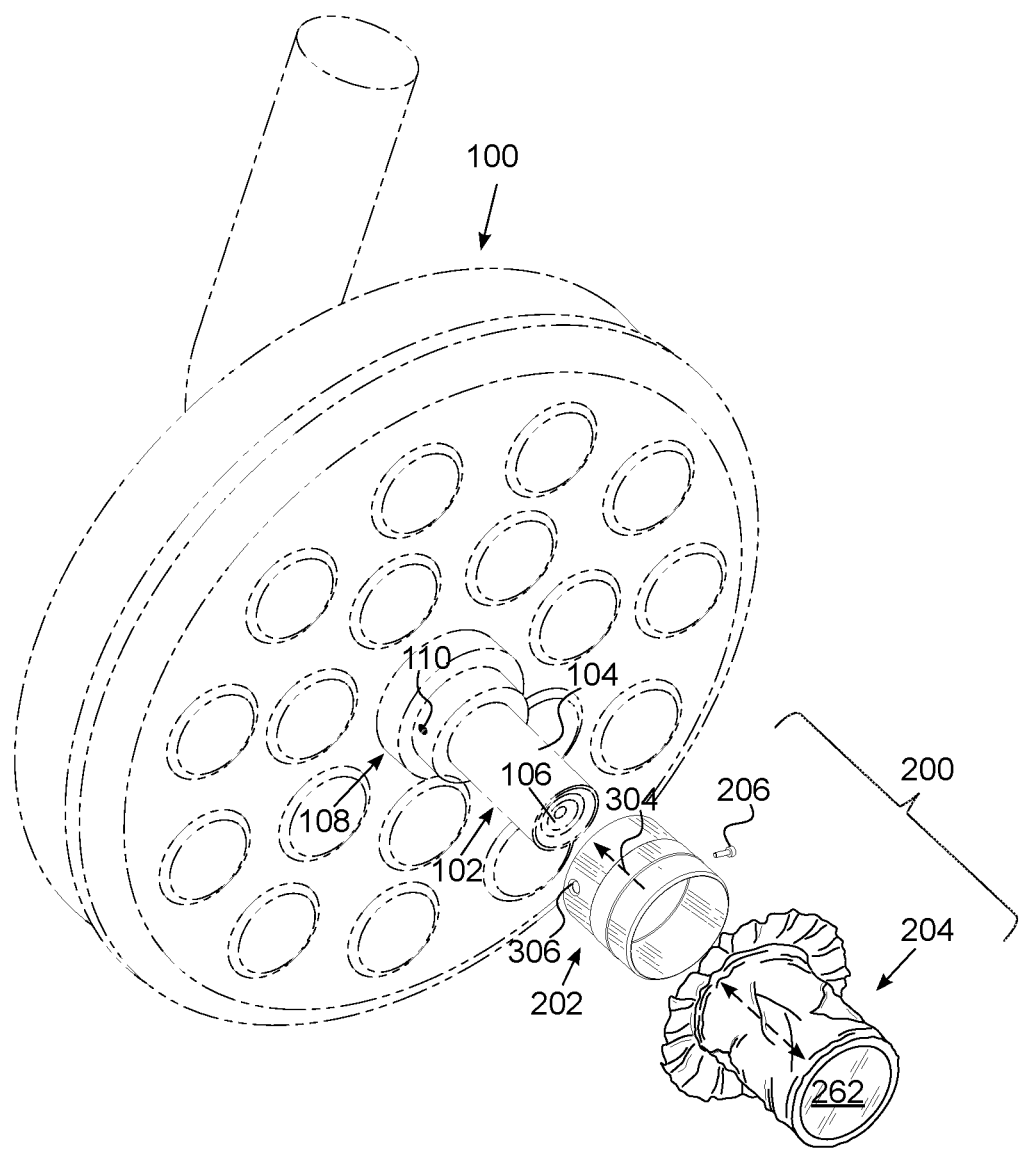
Figure 1D:
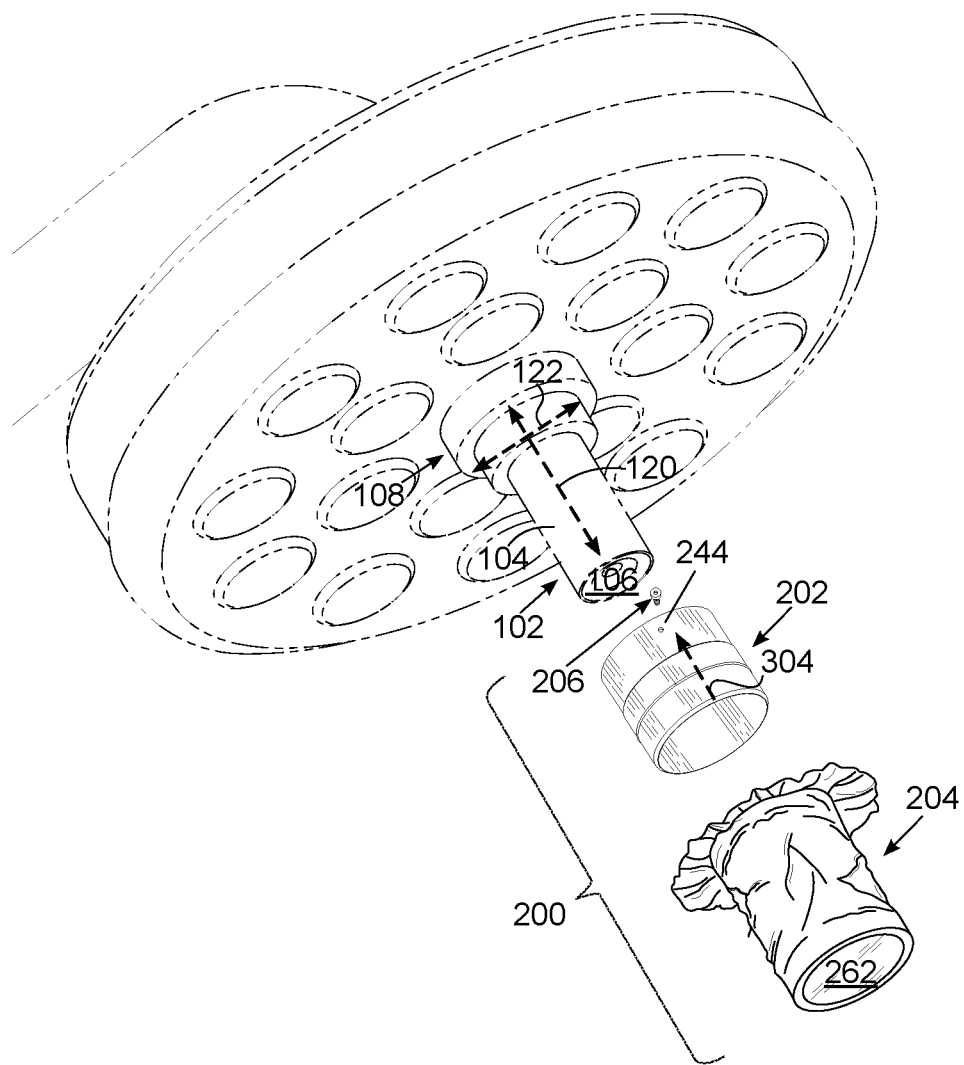
Figure 1E:
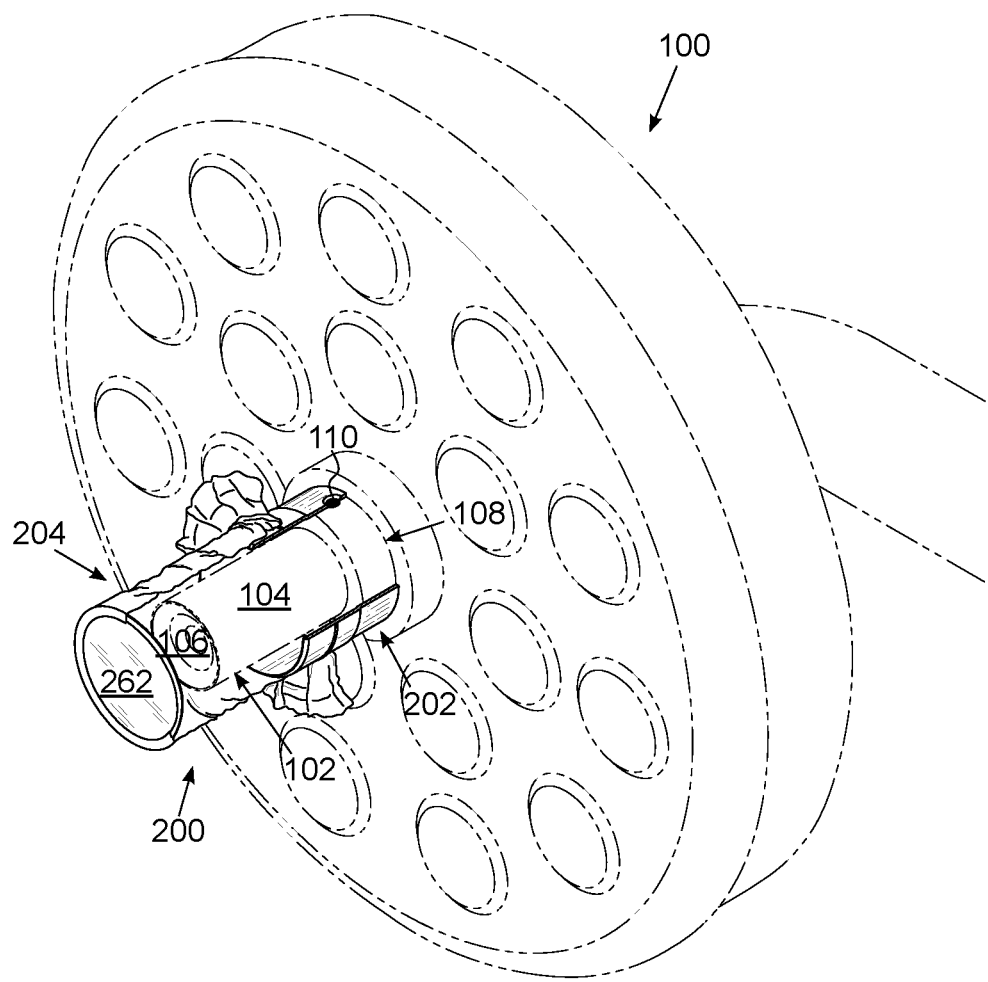

FIGS. 1A and 1B are non-limiting, exemplary perspective view illustrations of a fully assembled replacement cover assembly in accordance with one or more embodiments of the present invention, with FIGS. 1C and 1D an exploded views of the same and FIG. 1E a non-limiting, exemplary illustration of a partially cut, sectional view of the fully assembled replacement cover assembly shown in FIG. 1A. As illustrated in FIG. 1A to 1E, the present invention provides a surgical room camera replacement cover assembly 200 that includes an universal adapter interface unit 202 and a soft, pliable, disposable universal (and sterilized) replacement camera cover 204 that may detachably be coupled with universal adapter interface unit 202.

As best illustrated (in FIGS. 1C to 1E), a well known non-limiting, exemplary surgical light assembly 100 may include a surgical light camera 102 that has a camera body 104, a lens 106, and a connection section 108 with a fastener (or latching) mechanism 110. As illustrated in FIGS. 1A to 1E, universal adapter interface unit 202 of surgical room camera replacement cover assembly 200 in accordance with one or more embodiments of present invention is detachably connected with and secured on to surgical light assembly 100 by fastening mechanism 110. Soft, pliable, disposable universal (and sterilized) replacement camera cover 204 may then be detachably coupled with the already connected universal adapter interface unit 202.

FIGS. 2A to 2I are non-limiting, exemplary illustrations of a universal adapter interface unit in accordance with one or more embodiments of the present invention. Universal adapter interface unit 202 includes a first section 302 (or the adapter section) that is specifically configured to detachably couple with a particular surgical light fixture 100, and a second section 316 (the universal section) that is configured to universally, detachably couple with soft, pliable, disposable universal (and sterilized) replacement camera cover 204 in accordance with one or more embodiments of the present invention.

Before continuing further, it is very important to emphasize and understand that the drawings are to be used for the purposes of exemplary illustrations only and not in any way define the limits of the invention. For example, the drawings illustrate a very specific configuration of first section 302 (the adapter section) of universal adapter interface unit 202. That is, first section 302 is specifically configured and particularly adapted to correspondingly match and to detachably couple with the correspondingly matched (i.e., complementary) connection section 108 of the specifically illustrated surgical light camera 102 of surgical light fixture 100.

However, all existing surgical light assemblies and their associated camera equipment are unique, specifically manufactured by competing companies. Of course, as a result of this wide variations in differences in surgical light assemblies and their respective camera equipment, it would not be practical and, in fact, impossible to illustrate all existing different surgical light assemblies and their uniquely associated camera equipment. Therefore, in the same respect, it would not be practical and, in fact, also impossible to illustrate all possible variations of first section 302 (the adapter section) of universal adapter interface unit 202 of the present invention that may be configured and adapted to correspondingly match with existing different surgical light assemblies and their associated camera equipment. Accordingly, the drawings shown are merely provided for illustrative purposes for better understanding of the present invention and should not be limiting to specific surgical light fixture 100, surgical light camera 102, connection section 108, fastening mechanism 110, and a correspondingly matching first section 302 (the adapter section) of universal adapter interface unit 202 of the present invention shown. For example, if connection section 108 of surgical light camera 102 is square, pentagon, or any other shape, then first section 302 of universal adapter interface unit 202 of the present invention may be configured and adapted to correspondingly match with the shape of connection section 108 and fit to cover surgical light camera 102. As another example, connection section 108 of surgical light camera 102 may have other fastening mechanisms such as a radial array of plurality of biased buttons instead of the single biasing button (or spring latch button) 110 that is illustrated. In such an exemplary instance, first section 302 (the adapter section) of universal adapter interface unit 202 of one or more embodiment of the present invention may be configured to include complementary, corresponding set of radial array of apertures to accommodate the radial array of plurality of biasing buttons to detachably couple universal adapter interface unit 202 with surgical light camera 102. In yet another non-limiting, exemplary instance, connection section 108 of the surgical light camera 102 may use a snap or other latch or connection mechanism in which case, first section 302 of universal adapter interface unit 202 may comprise of snap or corresponding latch mechanism that snaps onto and detachably couples or latches with connection section 108 of surgical light camera 102. Therefore, it is imperative to understand that the drawings are to be used for the purposes of exemplary illustrations only, and should in no way be limiting.

To continue, as further illustrated in FIGS. 2A to 2I, first section 302 (the adapter section) of the universal adapter interface unit 202 includes an adapter mechanism (or coupling mechanism) that is configured to detachably couple with an associated fastening mechanism of a particular surgical light fixture. That is, first section 302 (or the adapter section) is specifically configured and particularly adapted to associate with a specifically corresponding connection section of a particular surgical light camera. This enables coupling universal adapter interface unit 202 with a particular surgical light fixture, but without modifying the surgical light fixture. Stated otherwise, first section 302 of universal adapter interface unit 202 of one or more embodiment of the present invention is configured and adapted to detachably couple with a surgical light fixture or camera in the same manner as any OEM camera cover is specifically and uniquely made to mate with its corresponding surgical light fixture or camera, with no modifications to surgical light fixture 100 or surgical light camera 102.

Accordingly, with the abovementioned arrangement, multiple universal adapter interface units 202 with different types of first sections 302 (adapter sections) that are uniquely configured and specifically adapted for detachable connection with different surgical light fixtures would be required. This would be particularly true for a hospital having multiple different types/makes/models of surgical light assemblies (including the uniquely associated surgical light camera) from multiple manufacturing companies.

As further illustrated, second section 316 (the universal section) of the universal adapter interface unit 202 is configured to universally, detachably couple with soft, pliable, disposable universal (and sterilized) replacement camera cover 204. Second section 316 includes a securing structure 310, which forms an engaging (or latching) surface structure on second section 316 to allow for detachable engagement of soft, pliable, disposable universal (and sterilized) replacement camera cover 204.

As further illustrated in FIGS. 2A to 2I, in this exemplary instance, first section 302 (or the adapter section) of universal adapter interface unit 202 is configured to include an interlock aperture 306 that accommodates the exemplary fastening mechanism 110 of surgical light camera 102. Universal adapter interface unit 202 is first placed on surgical light camera 102 by maneuvering it along path 304 (FIG. 1C) and orienting interlock aperture 306 to align with fastening mechanism 110. When fully inserted onto surgical light camera 102 (illustrated in FIGS. 1A and 1E), fastening mechanism 110 snaps into interlock aperture 306 of first section 302 of universal adapter interface unit 202, locking universal adapter interface unit 202 on surgical light camera 102.

As further illustrated, first section 302 of universal adapter interface unit 202 includes a first opening 320 with inner diameter 324, and interlock aperture 306, with first section 302 configured to detachably fit onto and mate with connection section 108 of surgical light camera 102. Exterior surrounding surface 230 of interlock aperture 306 has recessed portion (e.g., countersink) 232 formed from beveled rim, enabling an end of latched fastening mechanism 110 to extend out of interlock aperture 306 and be flush with exterior surface 234 of first section 302. This way, the latched fastening mechanism 110 may be pushed out of interlock aperture 306 and unlatched for detaching and removal of universal adapter interface unit 202. Interior surrounding surface 236 of interlock aperture 306 from periphery edge 240 of opening 320 and leading to the interlock aperture 306 itself is chamfered 238 (forming a channel) to guide fastening mechanism 110 for easy intersection and latching interlock with interlock aperture 306.

First section 302 of universal adapter interface unit 202 further includes an optional auxiliary redundancy engagement mechanism 242 that is used as backup in case of a failure of proper connection or engagement of universal adapter interface unit 202 with connection section 108 of surgical light camera 102 via a potentially failed engagement of fastening mechanism 110 and interlock aperture 306 combinations. In this non-limiting, exemplary instance, auxiliary redundancy engagement mechanism 242 may comprise of an opening 244 through which a fastener such as screw 206 is inserted, a tip 208 of which engages connection section 108 of surgical light camera 102 to frictionally secure universal adapter interface unit 202 with connection section 108 of surgical light camera 102.

As further illustrated, universal adapter interface unit 202 also includes second section 316 (the universal section) that is configured to enable detachable engagement or coupling of soft, pliable, disposable universal (and sterilized) replacement camera cover 204 of the present invention. In other words, second section 316 (or the universal section) with securing structure 310 enables soft, pliable, disposable universal (and sterilized) replacement camera cover 204 to couple with surgical light fixture 100 via universal adapter interface unit 202. This way, the OEM cover is no longer needed, and instead, soft, pliable, disposable universal (and sterilized) replacement camera cover 204 of the present invention is used, and disposed of after a single use. This can lower costs and improve efficiency of operating room use. Of course, soft, pliable, disposable universal (and sterilized) replacement camera cover 204 of the present invention is sterilized before it is used, packaged, and then disposed of after use. It should be noted that universal adapter interface unit 202 need not be sterilized because it is generally considered as part of non-sterile field or zone of an operating room.

Second section 316 of universal adapter interface unit 202 includes a second opening 312 with an inner diameter 314. It should be noted that the configurations of first section 302 (adapter section) and second section 316 (universal section) are independent of one another. That is, first section 302 (adapter section) is specifically configured to mate with a corresponding connection section of a surgical light camera and may comprise of any shape or diameter (or cross-sectional length). On the other hand, second section 316 (the universal section) of universal adapter interface unit 202 is configured to mate with soft, pliable, disposable universal (and sterilized) replacement camera cover 204 of the present invention with its own unique connection characteristics (the details of which are provided below).

Figure 2A:
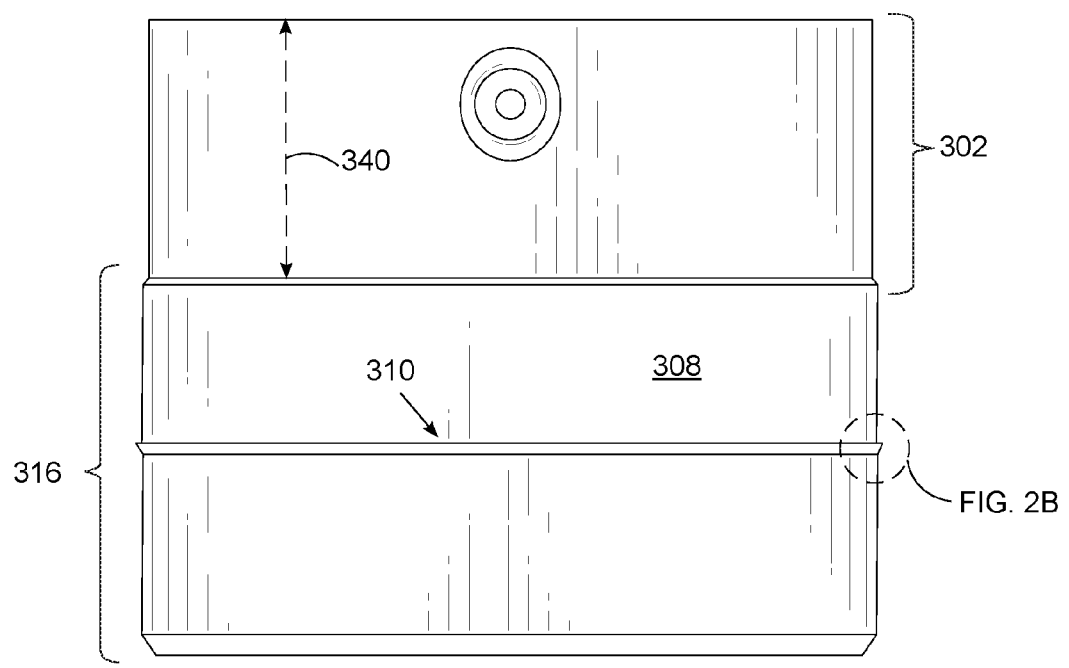
FIGS. 2A to 2I are non-limiting, exemplary illustrations of a universal adapter interface unit in accordance with one or more embodiments of the present invention.
Figure 2B:
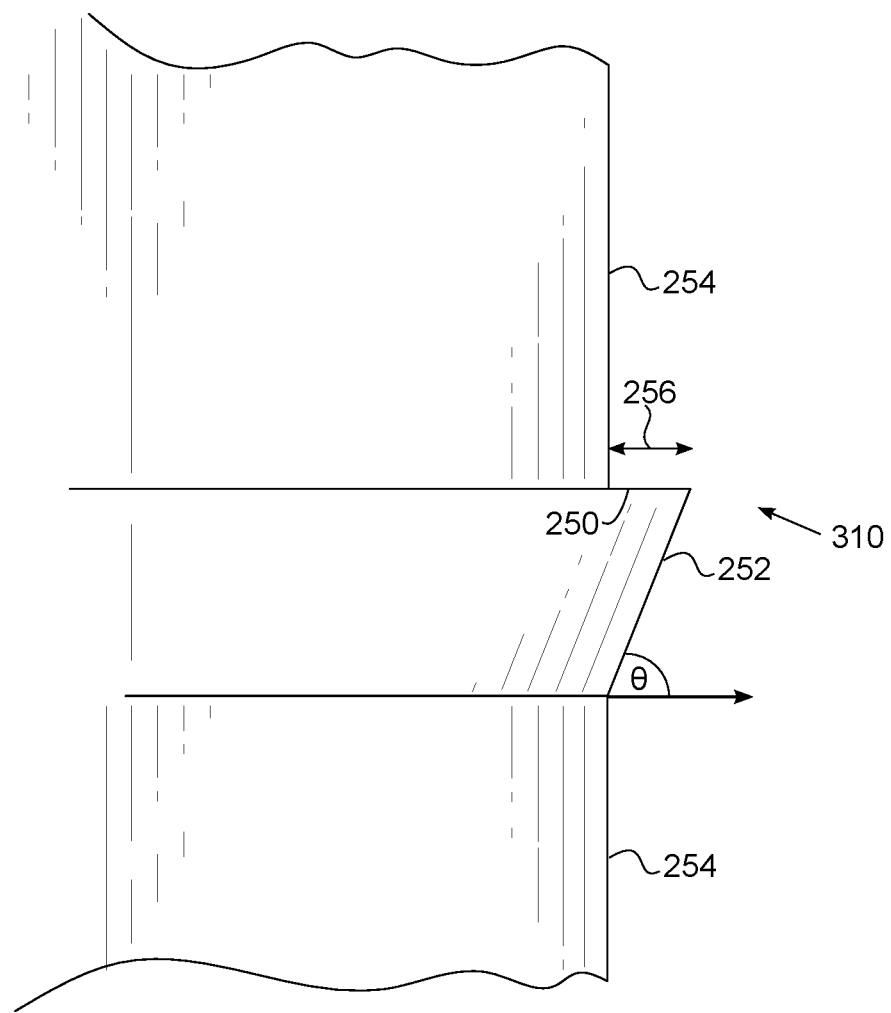
Figure 2C:
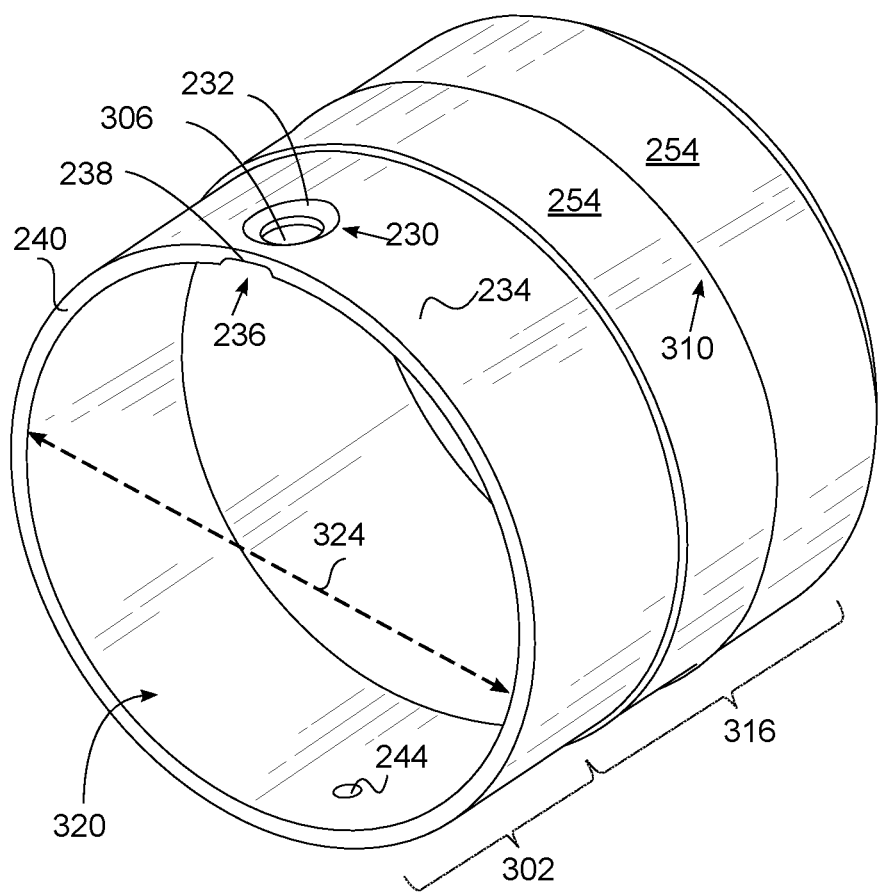
Figure 2D:
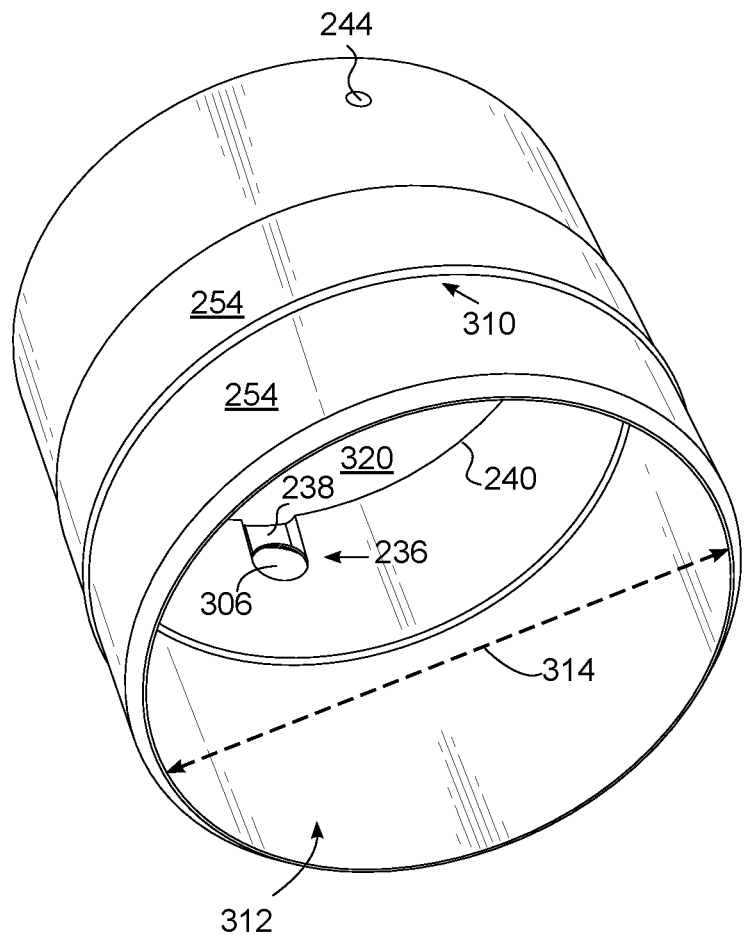
Figure 2E:
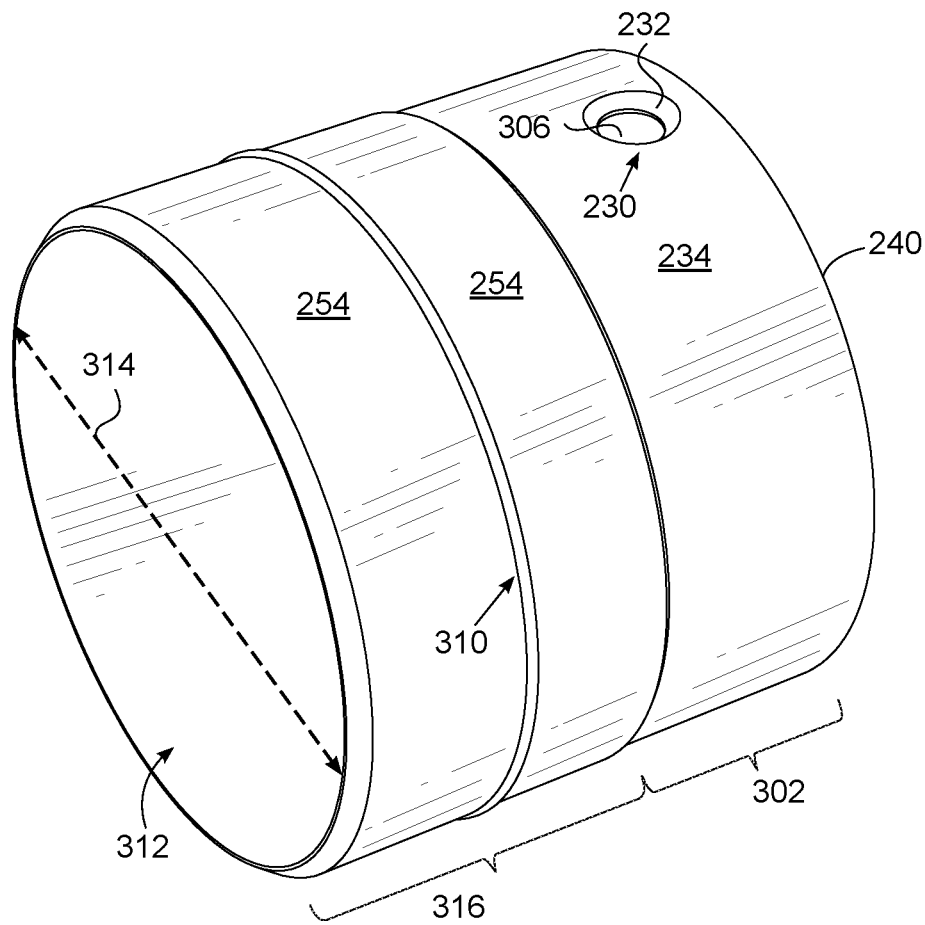
Figure 2F:
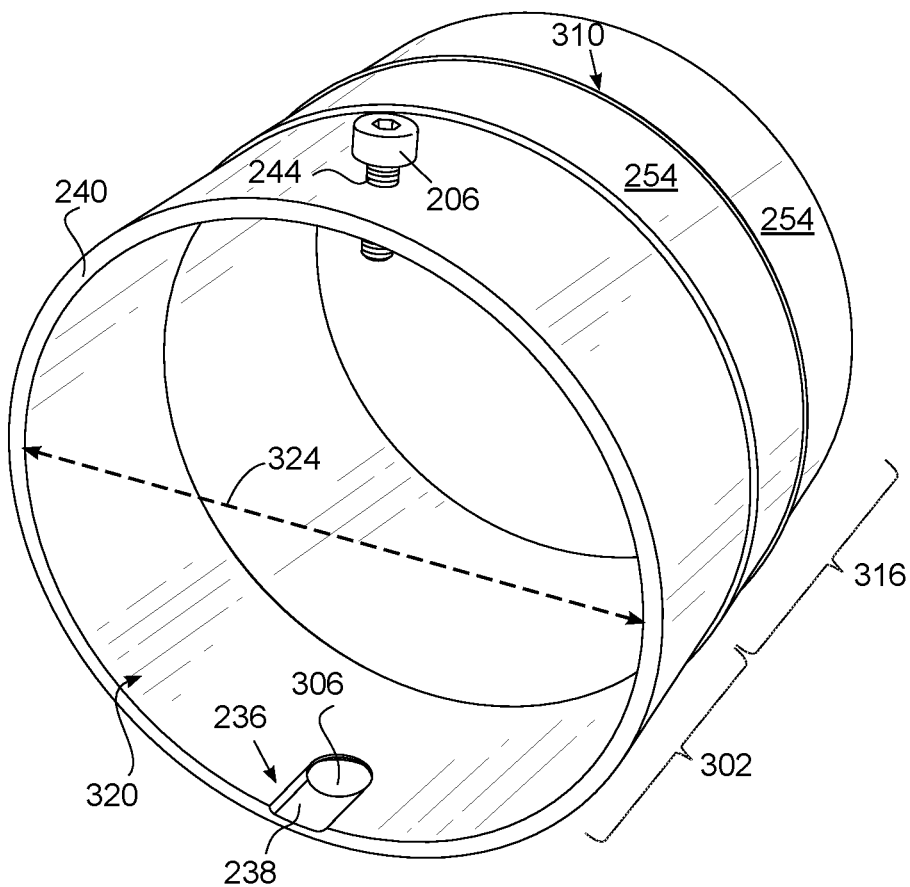
Figure 2G:
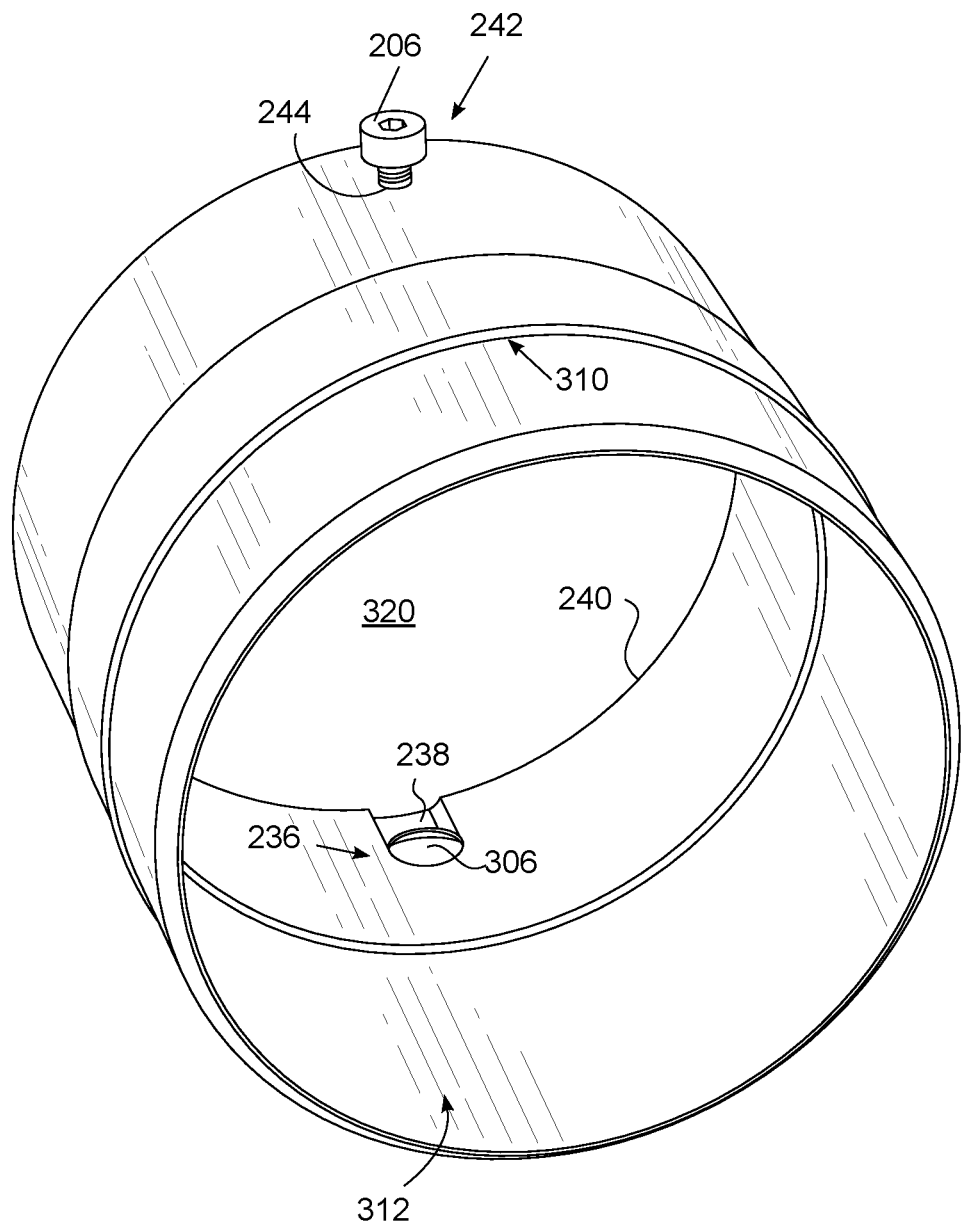
Figure 2H:
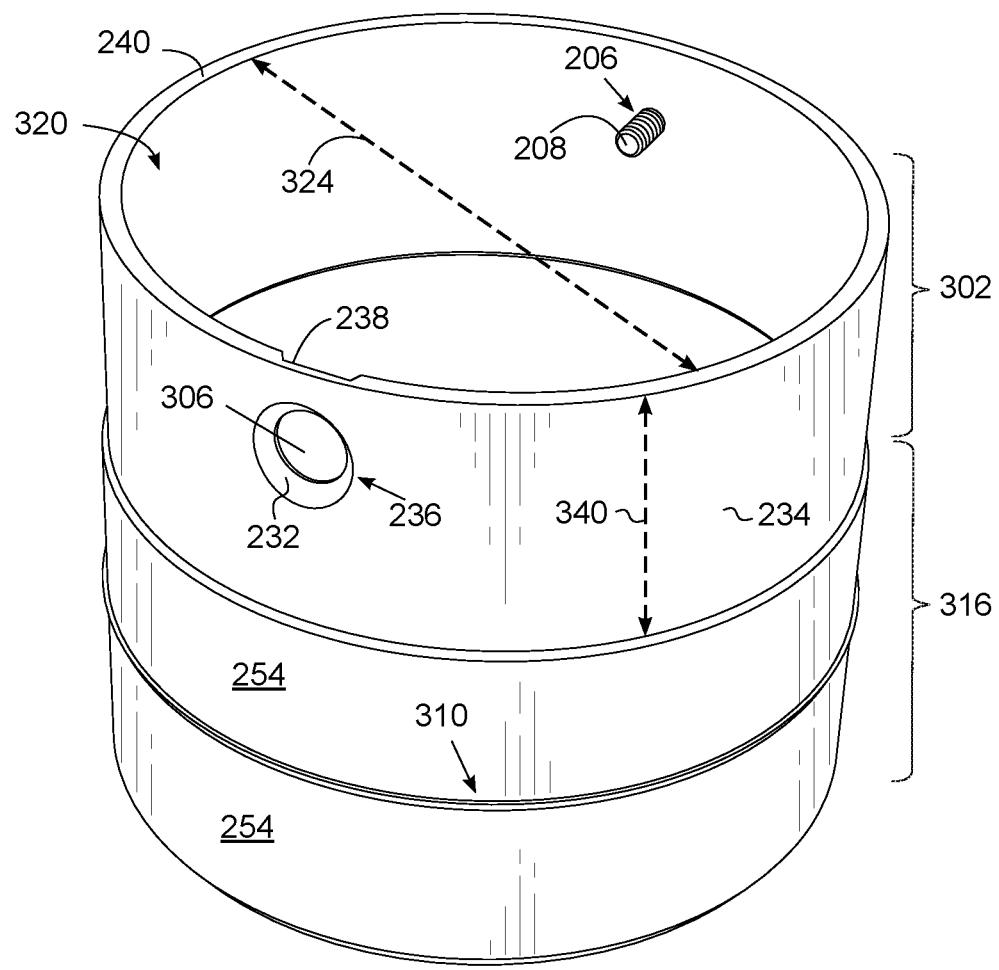
Figure 2I:
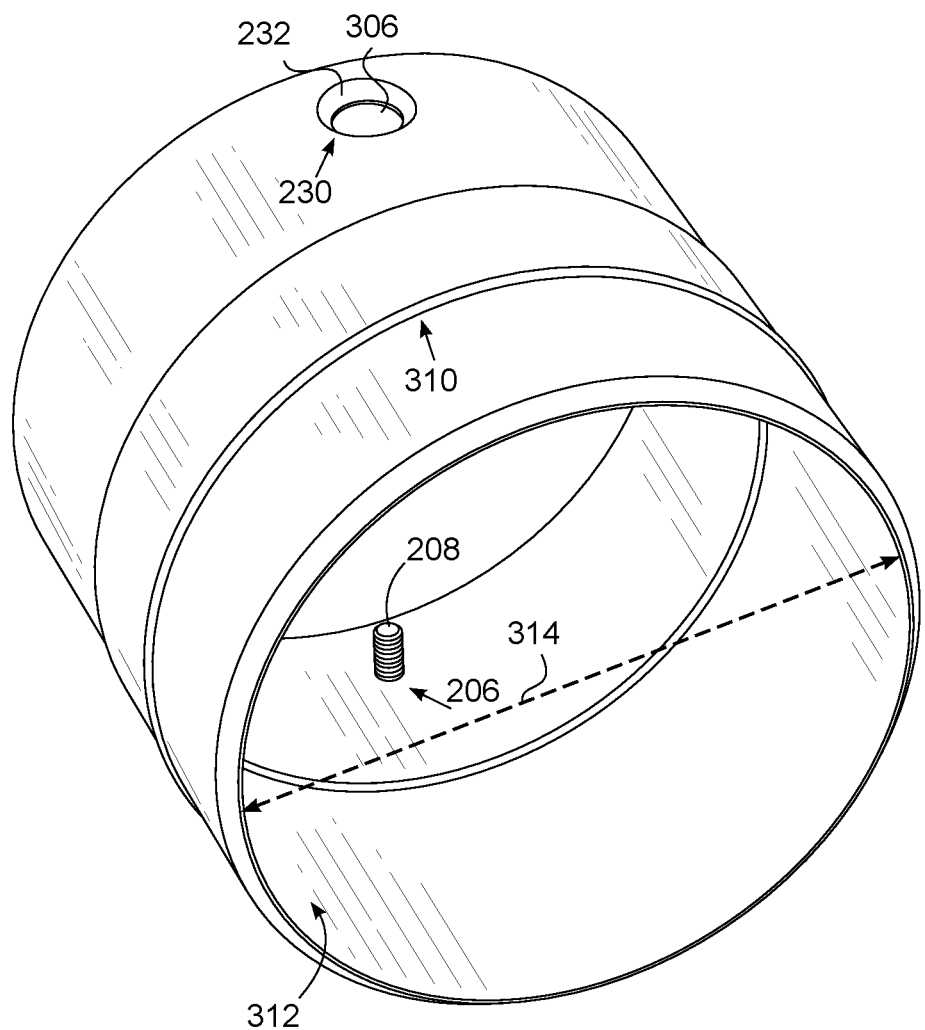

Securing structure 310 of second section 316 forms an engagement (or latching) surface structure that is comprised of a circumferential ledge 250, a base 252 of which protrudes at an angle θ (about 68°) from an outer surface 254 of second section 316 at distance D (illustrated by arrow 256 in FIG. 2B). Securing structure 310 provides a fixed engagement point that is indicative of a proper (detachable) connection of soft, pliable, disposable universal (and sterilized) replacement camera cover 204 with universal adapter interface unit 202. In other words, securing structure 310 also functions as a coupling or engagement index, functioning as a "maker" or "index" coupler that enables users to "feel" the correct mounting position of soft, pliable, disposable universal (and sterilized) replacement camera cover 204 as cover 204 is detachably mounted and secured onto universal adapter interface unit 202.

Soft, pliable, disposable universal (and sterilized) replacement camera cover 204 in combination with universal adapter unit 202 when fully assembly, provide an indication to end-users that cover 204 has mounted at a proper engagement position in accordance with one or more embodiments of the present invention. In other words, manner of mounting soft, pliable, disposable universal (and sterilized) replacement camera cover 204 is universally consistent at the engagement point 310 in accordance with one or more embodiments, obviating potential improper mounting that may lead to varying distances between the viewing area of the cover and that of camera lens, which would provide inconsistent focusing quality of camera (assuming the cover viewing area and camera lens are still aligned). Further, securing structure 310 also obviates potential slip-off of soft, pliable, disposable universal (and sterilized) replacement camera cover 204 during surgery due to improper installation. Different variations of securing structure 310 and its commensurately corresponding, complementary engagement structure on soft, pliable, disposable universal (and sterilized) replacement camera cover 204 are possible, and should not be limiting to the illustrated ledge 250.

FIGS. 3A to 3L are non-limiting, exemplary illustrations of soft, pliable, disposable universal (and sterilized) replacement camera cover in accordance with one or more embodiments of the present invention. As illustrated in FIGS. 1A to 3L, soft, pliable, disposable universal (and sterilized) replacement camera cover 204 has a first, overall expanded height 440 (best shown FIGS. 3A to 3E, and 3J) for use, and a second, overall collapsed height 442 (best shown in FIGS. 3F to 3H) for storage in a small, compact package.

As further detailed below, soft, pliable, disposable universal (and sterilized) replacement camera cover 204 is comprised of a lower section 400 that generally falls within a sterile field of an operating room. Lower section 400 includes a viewing section 404 that provides a view of an operative field for surgical light camera 102, with the viewing section 404 including a cover lens 262. A diameter 430 of viewing section 404 may generally be of any span so long as the view of cameral lens 106 is not blocked.

Figure 3A:
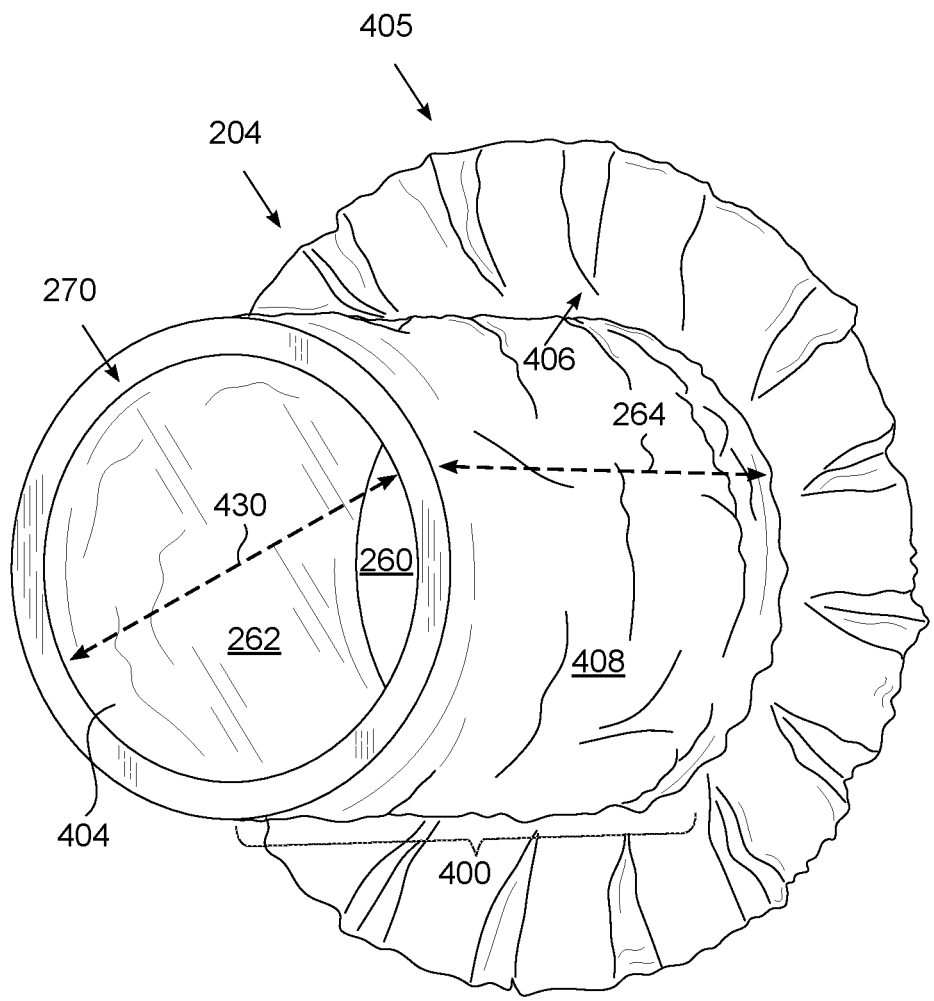
FIGS. 3A to 3L are non-limiting, exemplary illustrations of soft, pliable, disposable universal (and sterilized) replacement camera cover in accordance with one or more embodiments of the present invention.
Figure 3B:
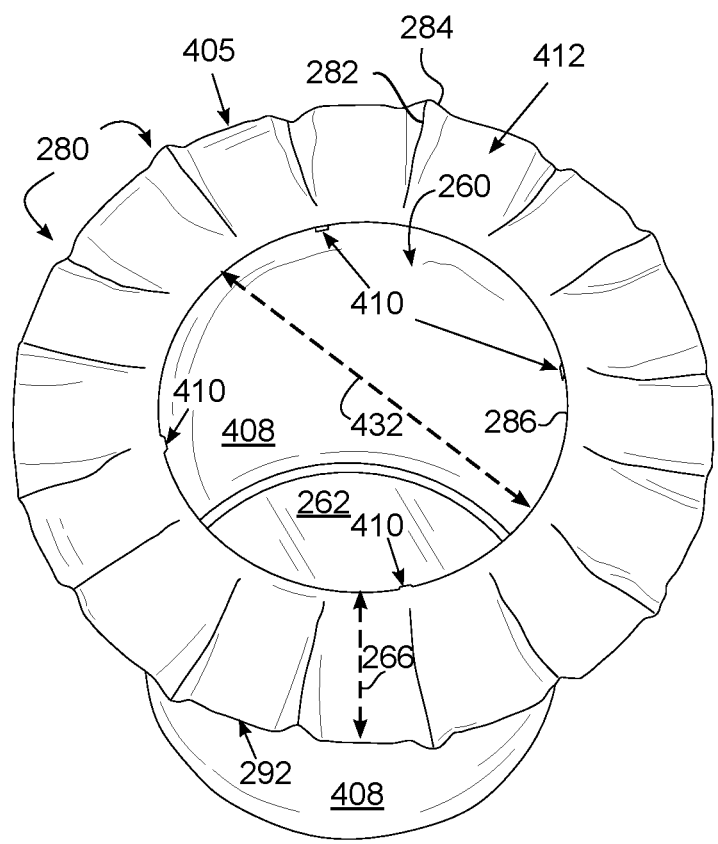
Figure 3C:
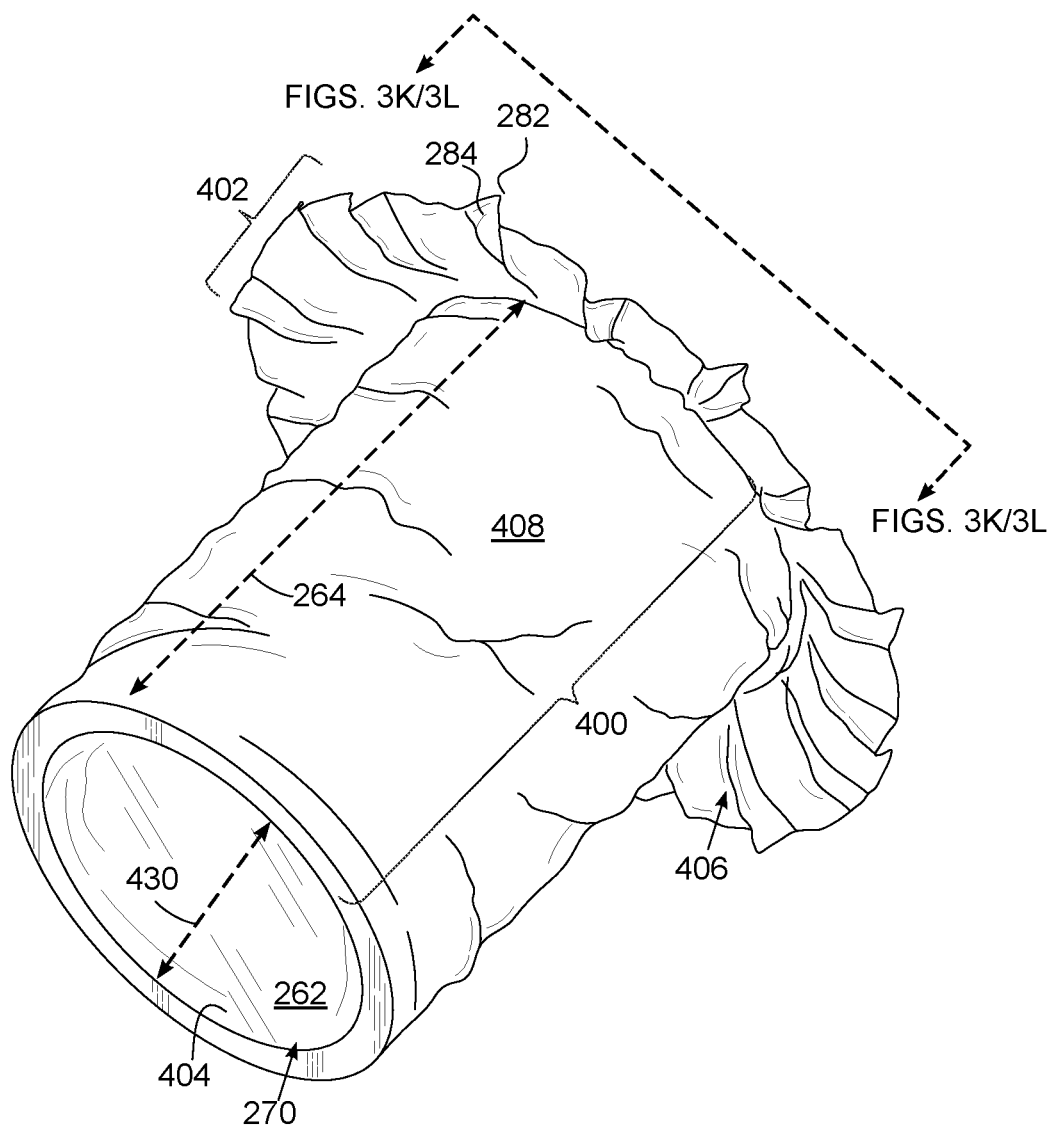
Figure 3D:
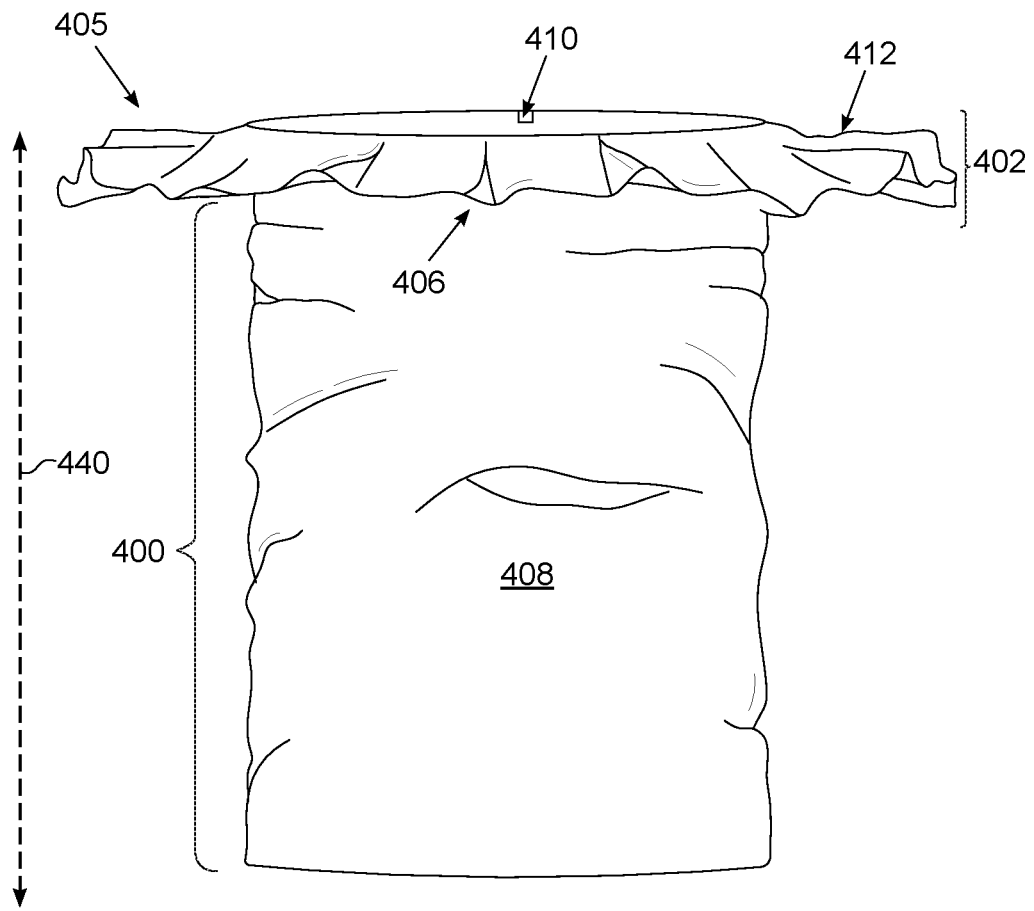
Figure 3E:
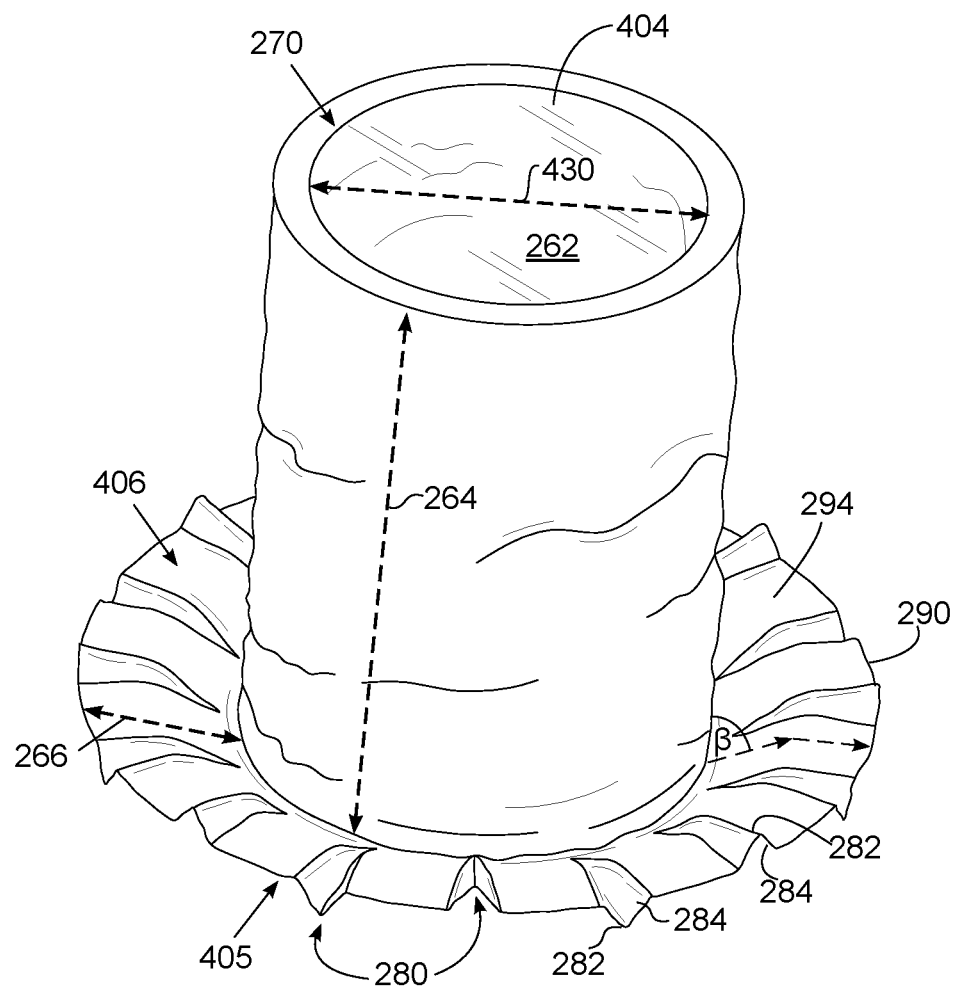
Figure 3F:
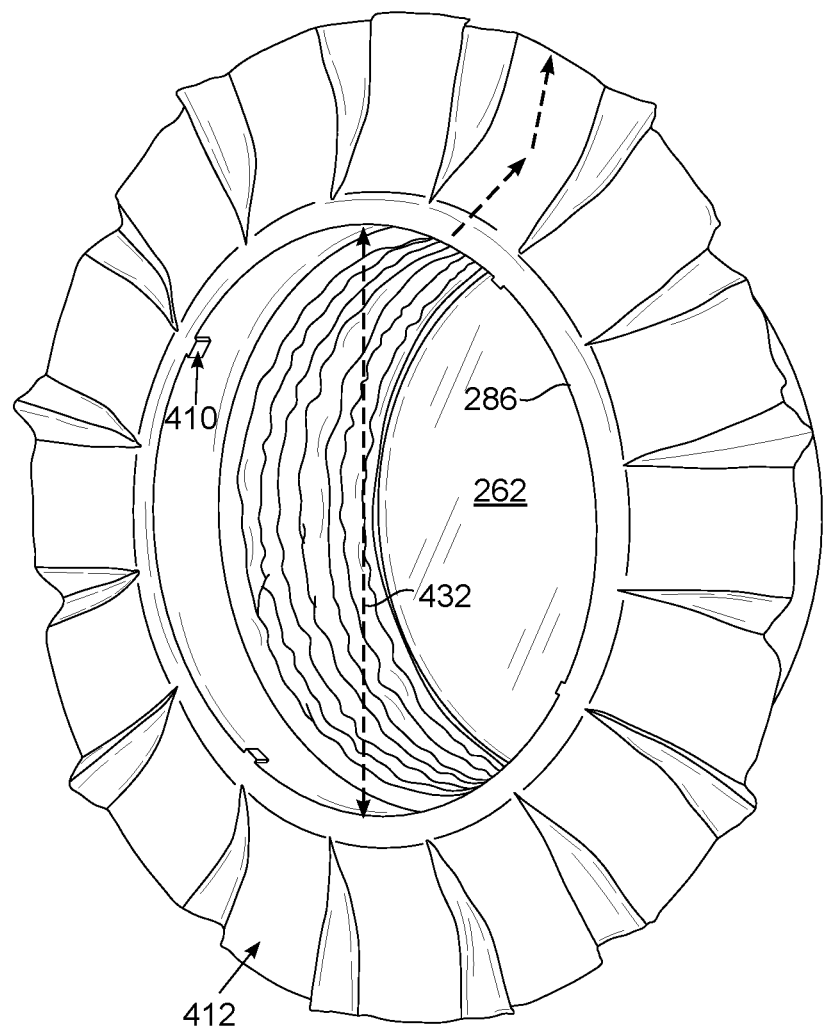
Figure 3G:
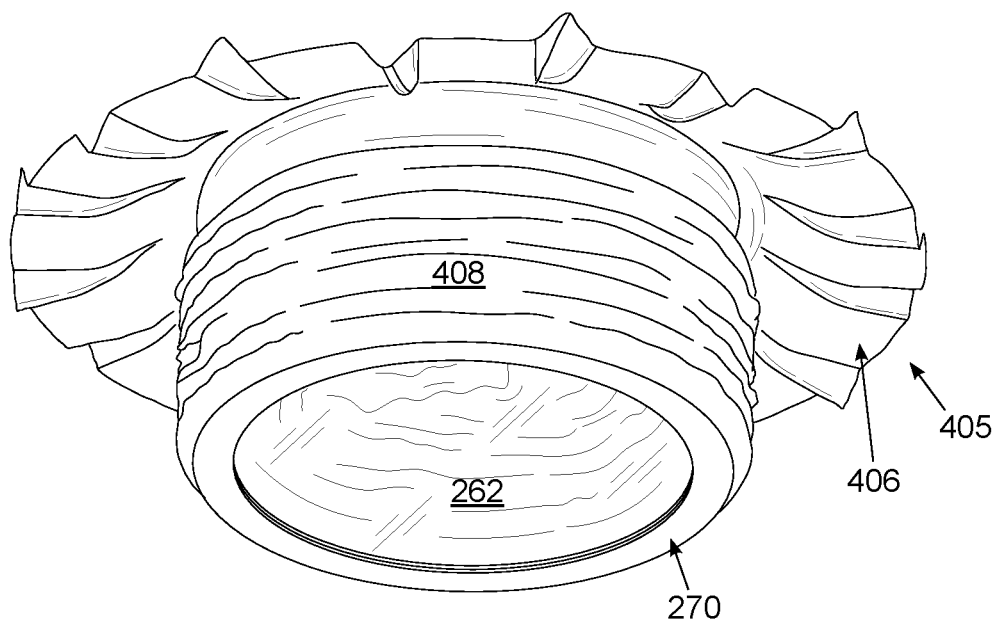
Figure 3H:
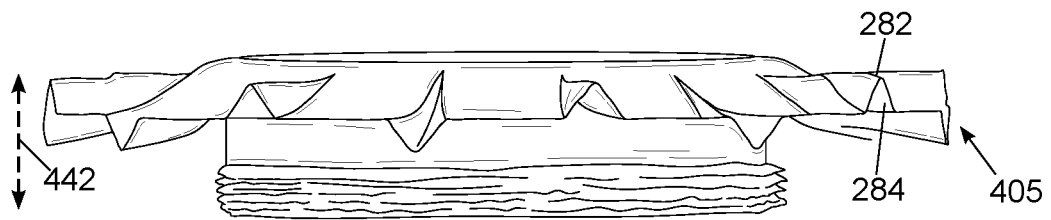
Figure 3I:
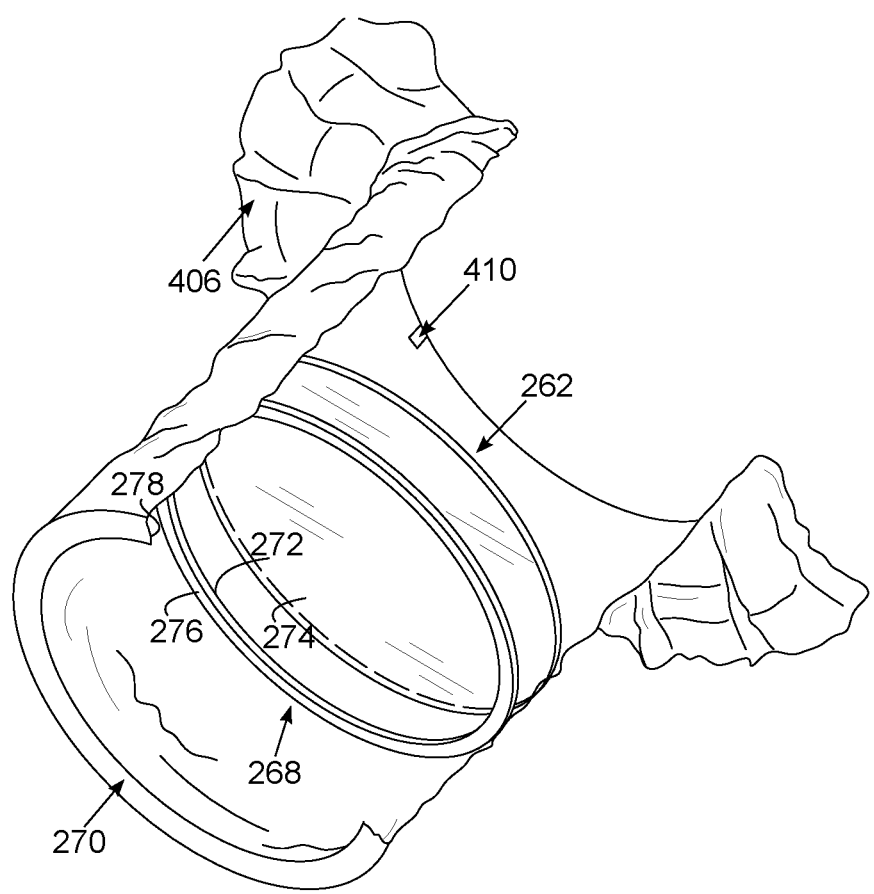
Figure 3J:
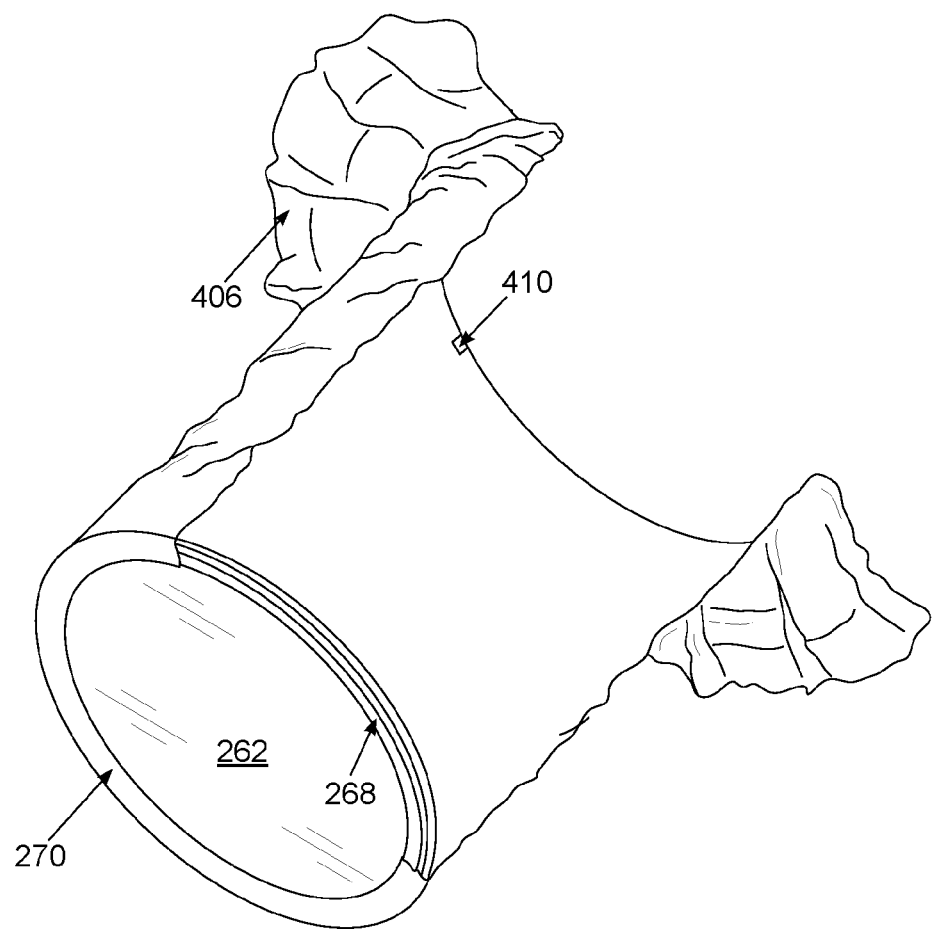

As best illustrated in FIGS. 3I and 3J, cover lens 262 may be comprised of polycarbonate (preferred), polypropylene (of different grade), polystyrene, with cover lens 262 coupled with soft, pliable, disposable, universal replacement camera cover 204 by a double sided adhesive member 268 at lens capture flange 270, which defines viewing area 404. Lens capture flange 270 may be die cut from the rest of cover 204. Use of a double-sided adhesive 268 versus other types of coupling (e.g., ultra sonic welding) is preferred due to large differences in thicknesses between the polycarbonate cover lens 262 (which is about 0.060 inches) and the lens capture flange 270 (which is about 0.002 inches or greater). In general, double-sided adhesive 268 may have an annular ring form, with one side 272 of adhesive 268 attached to a bottom (outside facing) periphery 274 of cover lens 262, while the other side 276 of adhesive 268 coupled to interior facing side 278 of lens capture flange 270 (as best show in FIG. 3I).

Lower section 400 further includes a body 408 that houses and provides protective covering for surgical light camera 102. Body 408 is generally cylindrical, with sufficient height 264 and diameter 432 to enable insertion and full, protective covering of surgical light camera 102. Body 408 houses and provides a sterile, protective covering for surgical light camera 102. In this exemplary instance, body 408 is exemplarily configured as substantially cylindrical, with sufficient height 264 and inner diameter 432 to enable insertion and full coverage of surgical light camera 102. It is imperative to note that lower section 400 may be of any shape and size, and should not be limited to the illustrated cylindrical configuration shown, so long as cover 204 fully covers the more expensive and costly surgical light camera 102. Accordingly, any cross-section configuration with any length with sufficient span that would not block the view of the camera lens 106 and that would allow surgical light camera 102 to fit within body 408 may be used. For example, body 408 may comprise of a cone structure with a wider top (near barrier 405) or wider bottom (near viewing section 404). Accordingly, cover 204 of the present invention should not be limited to the illustrated right-cylindrical configuration with a substantially uniform circular profile along height 264 of body 408. In addition, the fully expanded overall height 440 of cover 204 may also vary to accommodate a height surgical light camera 102, but collapses into a very compact form to an overall collapsed height 442 for small, light packaging for delivery and storage.

Soft, pliable, disposable universal (and sterilized) replacement camera cover 204 is further comprised of an upper section 402 that generally falls within a non-sterile field of the operating room and has a barrier 405 (i.e., flange) in the form an annular disc flange with sufficient span 266 to prevent and block access into the non-sterile field. Barrier 405 functions to limit a grip of a user to within a sterile field, with barrier 402 having stiffener structures 266 to provide sufficient stiffness that facilitates to prevent barrier from substantial flexing during normal operation and use of cover 204.

Barrier flange 405 includes a first side 406 that is within the sterile field section and a second side 412 that faces the non-sterile field section. The overall width 266 of annular flange (that constitutes barrier 405) must be of sufficient span to provide a stop for the hand grip, and prevent and block the hand of the user to pass or move and slip into the non-sterile field (or upper section 402). However, it must not be too wide to block light from the surgical lights to create a "shadow" on the patient. Preferably, the overall diameter 266 may have a span of about 1.25 inch to about 1.5 inches.

As further illustrated, barrier 405 may comprise of stiffeners 280. Stiffeners 280 are comprised of non-uniform surfaces in a form of ridges that add strength and stiffness to barrier 405, greater than its actual gauge (the strength gauge of barrier 405). The number and spacing of stiffeners 280 may be varied. As illustrated, reinforcing ridges 280 are comprised of protuberances and corresponding complementary recesses (cavities, grooves, etc.) on barrier 405, forming embossments on one side of barrier 405 and corresponding complementary impressions on the other side of barrier 405 (i.e., an embossment 282 in one side is a depression 284 on the opposite side).

As best illustrated in FIG. 3E, barrier 405 has a curved cross-sectional profile, where a first side 406 of barrier 405 that falls within the sterile field is generally convex, and a second side 412 of barrier 405 is generally concave. That is, annular disc flange 405 progressively slopes from an inner periphery 286 of opening 260 at an angle β of about 60° (which also defines an inner diameter 288 of annular disc flange 405) to a higher elevation at first side 406 (and lower elevation at second side 412), and is generally flat at an outer periphery 290 that defines an outer diameter 292 of the curved cross-sectional profile.

The configured curved structure (especially at inner diameter 288 with lower elevation at first side 406) prevents barrier 405 from folding and user hand from slippage into the non-sterile field. For example, if a user over exerts in trying to mount cover 204, the curved structure provides added resiliency that acts against the over exertion. The hand must travel "up" the sloped curved structure against the pull of the gravity and further, the lower elevation (at first side 406) provides the resiliency to prevent barrier 405 from bending, which prevents the hand to slip into the non-sterile filed. The hand of the user when mounting cover 204 is generally positioned or "tucked" underneath the curved sloping portion near inner diameter 288 of barrier 405, with the "apex" 294 of the curve (first side 406) surrounding the peripheries of the index finger, palm, and thumb of the user. If the barrier 405 were to be straight (not preferred), potential of slippage would exist if users over exert cover 204 during mounting.

Figure 3K:
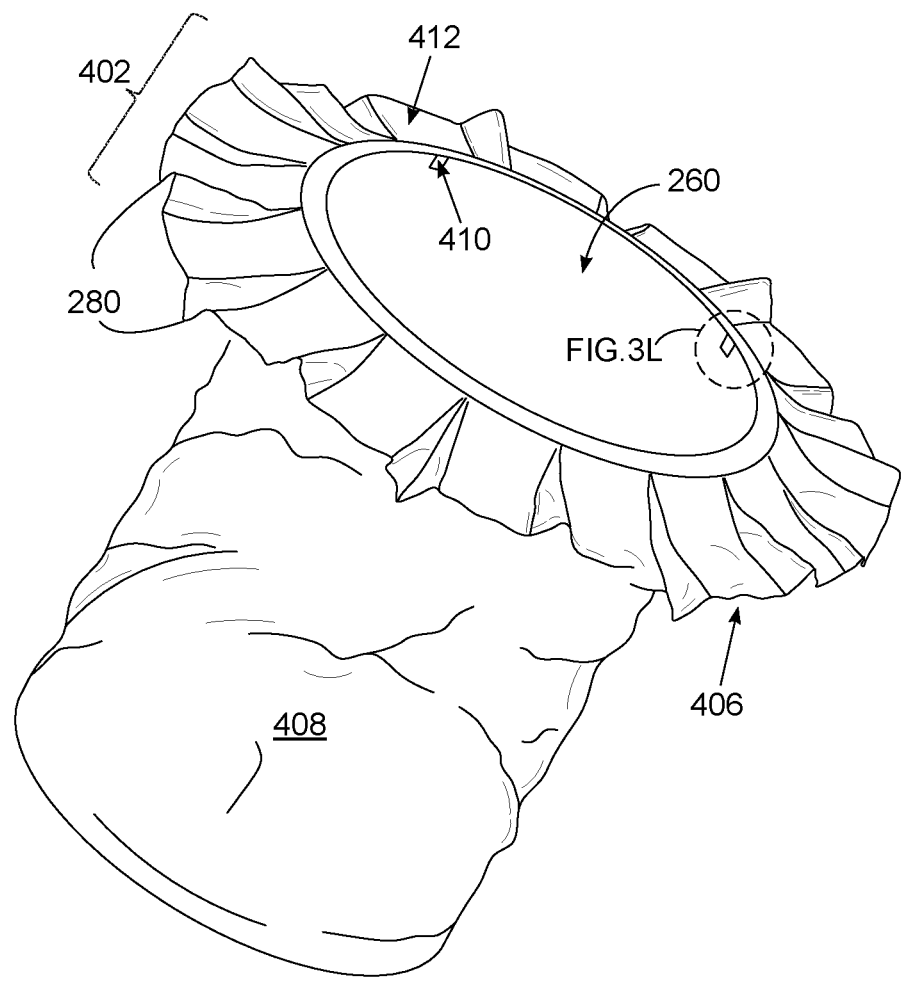
Figure 3L:
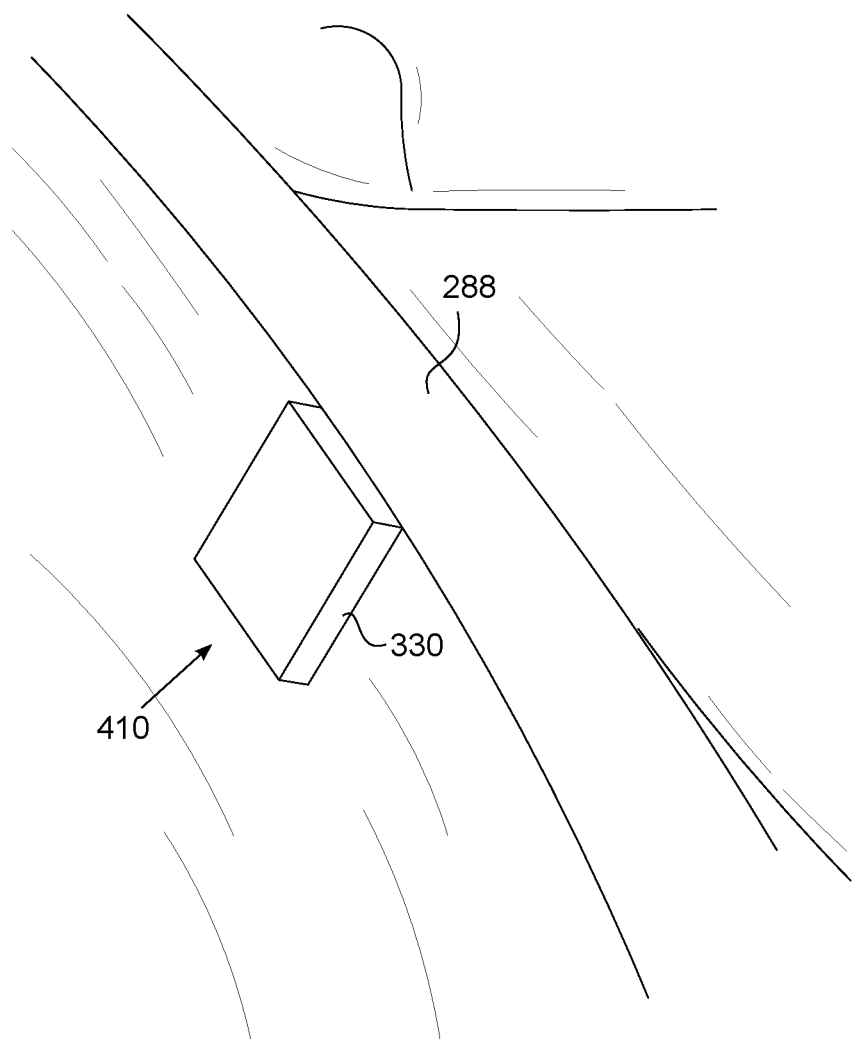

As best illustrated in FIGS. 3K and 3L, upper section 402 of soft, pliable, disposable, universal replacement camera cover 204 includes engagement members 410 that couples with securing structure 310 of second section 316 of universal adapter interface unit 202. In this non-limiting, exemplary instance, universal engagement members 410 are in a non-limiting, exemplary form of tabs that engage securing structure 310 of universal adapter interface unit 202. Securing structure 310 provides a fixed connection point that functions as indexing or marker feature that is indicative of a proper connection point of the soft, pliable, disposable, universal replacement camera cover 204 with universal adapter interface unit 202. The index aspect of securing structure 310 enables users to "feel" the correct mounting position of cover 204. Accordingly, soft, pliable, disposable, universal replacement camera cover 204 in combination with a universal adapter interface unit 202 when fully assembly, provide an indication to end-users that the cover has mounted at a proper engagement position in accordance with one or more embodiments of the present invention. Engagement members 410 have a thickness 330 of about less than or equal to 0.100 inches, which protrudes from inner diameter 288 of opening 260 inward as best illustrated in FIG. 3L.

It should be noted that other types of connection or engagement mechanisms that enables soft, pliable, disposable universal (and sterilized) replacement camera cover 204 to detachably couple with universal adapter interface unit 202 may be used so long as an indication is provided to end users that the engagement of soft, pliable, disposable universal (and sterilized) replacement camera cover 204 with universal adapter interface unit 202 is at a proper position and orientation. Further, the cross-sectional span 432 of the top opening 430 of soft, pliable, disposable universal (and sterilized) replacement camera cover 204 should be commensurate with the associated universal adapter interface unit 202 (i.e., second section 316) with which it is detachably coupled.

Figure 4A:
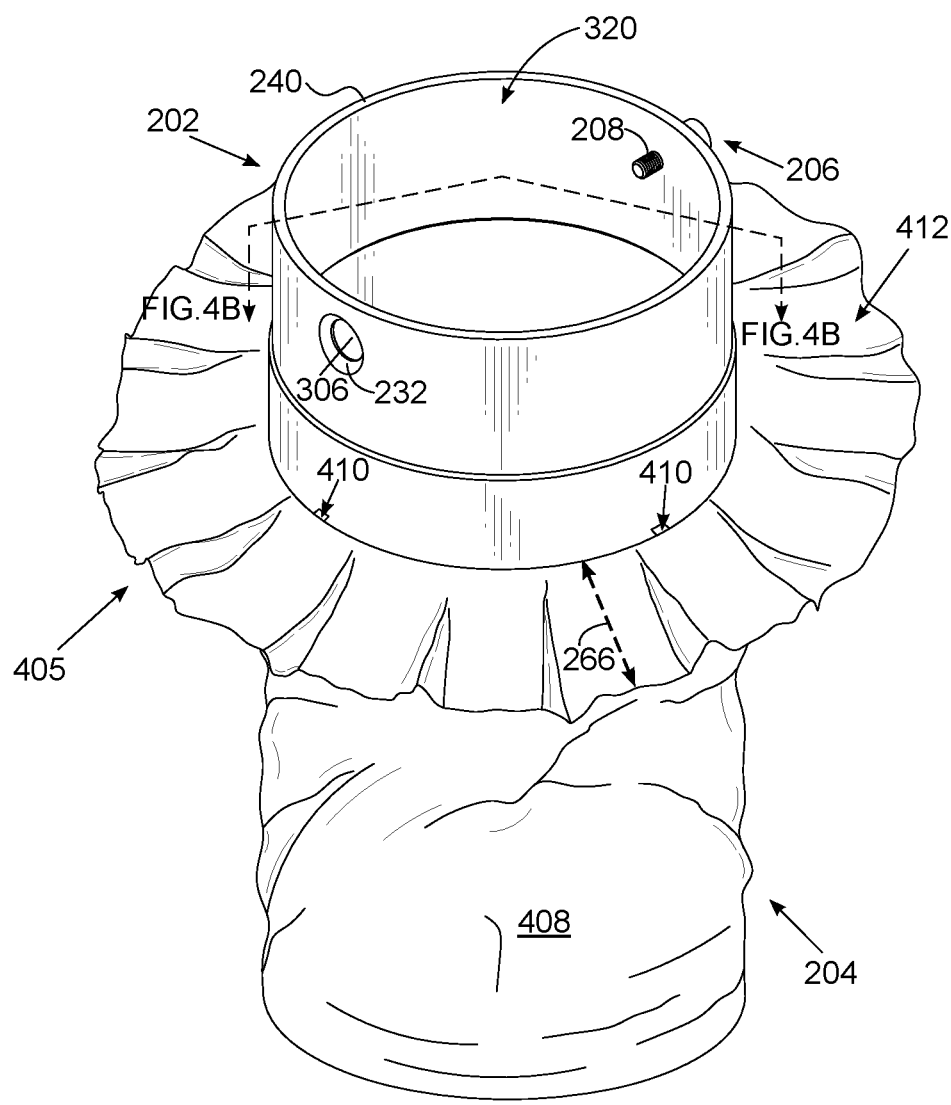
FIGS. 4A to 4H are non-limiting, exemplary illustrations, progressively illustrating a non-limiting, exemplary method of assembly (mounting) of soft, pliable, disposable universal (and sterilized) replacement camera cover onto universal adapter interface unit in accordance with one or more embodiments of the present invention.
Figure 4B:
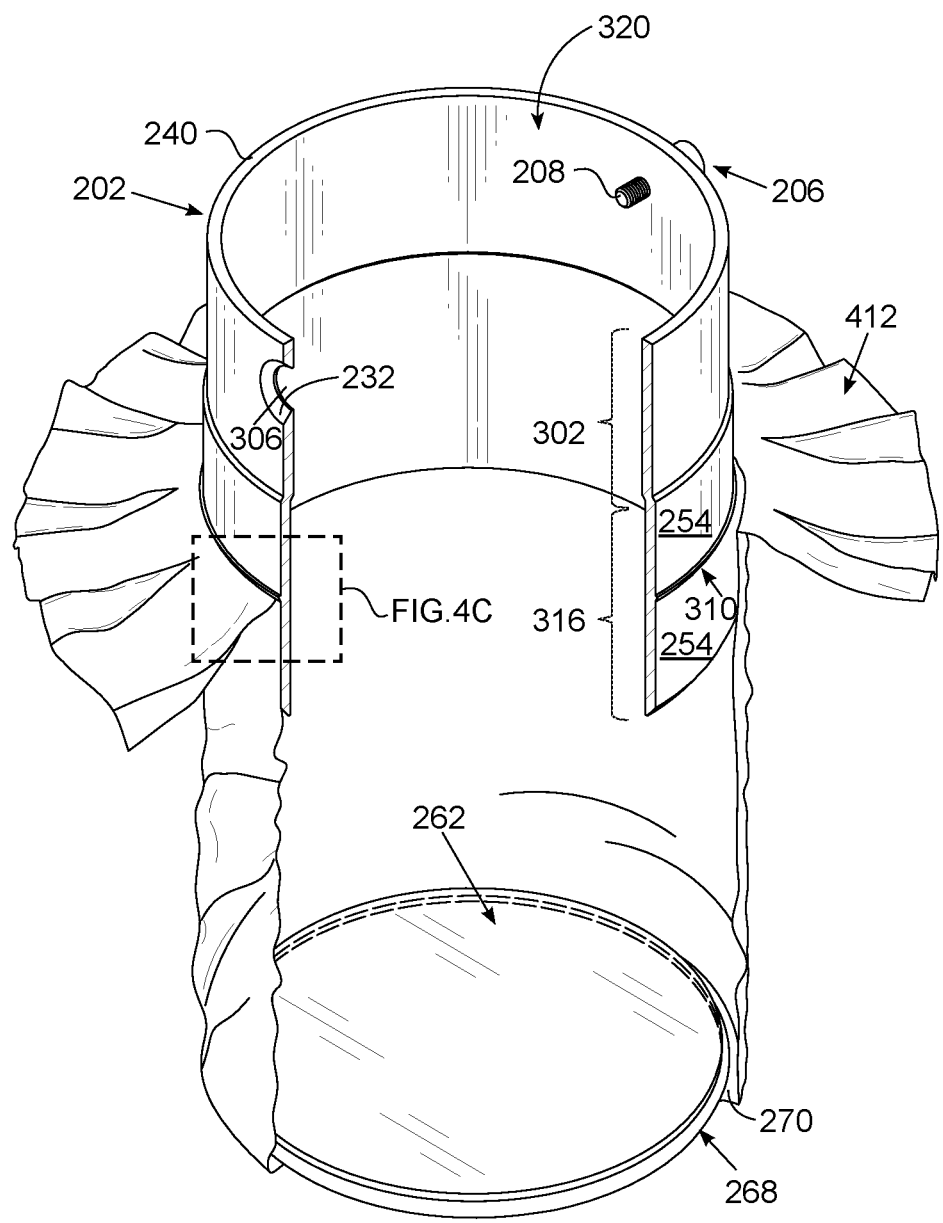
Figure 4C:
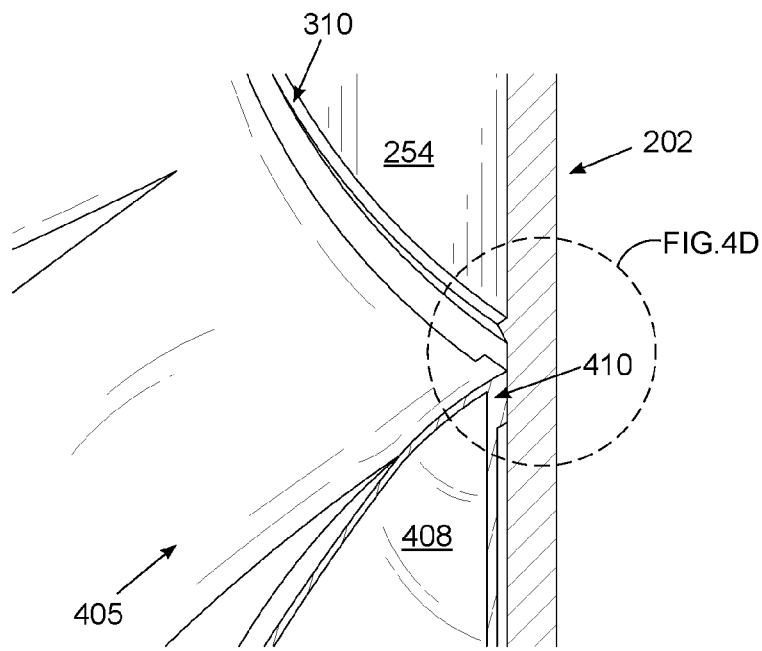
Figure 4D:
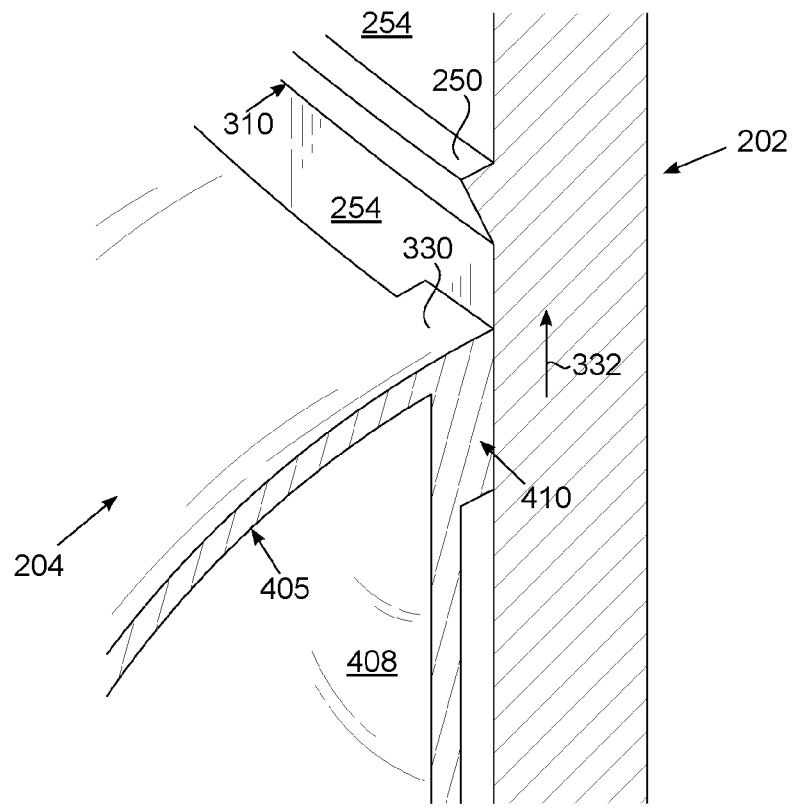

FIGS. 4A to 4H are non-limiting, exemplary illustrations, progressively illustrating a non-limiting, exemplary method of assembly (mounting) of soft, pliable, disposable universal (and sterilized) replacement camera cover onto universal adapter interface unit in accordance with one or more embodiments of the present invention. FIG. 4A is a non-limiting, exemplary illustration of a fully assembled (mounted) soft, pliable, disposable universal (and sterilized) replacement camera cover 204 on universal adapter interface unit 202 in accordance with one or more embodiment of the present invention. FIG. 4B a sectional view taken from FIG. 4A, but with soft, pliable, disposable universal (and sterilized) replacement camera cover 204 not fully assembled. That is, engagement members 410 of upper section 402 of soft, pliable, disposable universal (and sterilized) replacement camera cover 204 is partially mounted on universal adapter interface unit 202, just below securing structure 310 of universal adapter interface unit 202 (as best illustrated in the enlarged FIGS. 4C and 4D) and in process of being pushed up towards the securing structure 310 as shown by arrow 332.

Figure 4E:
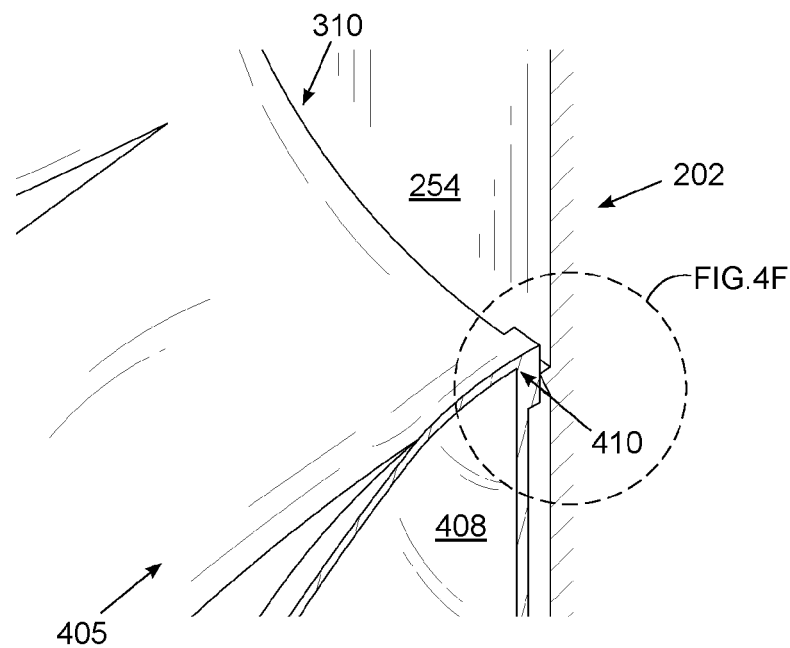
Figure 4F:
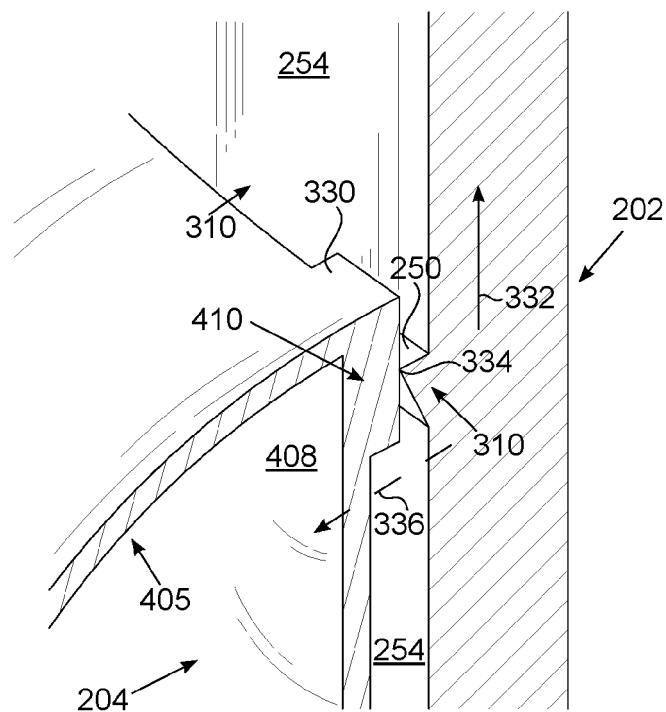
Figure 4G:
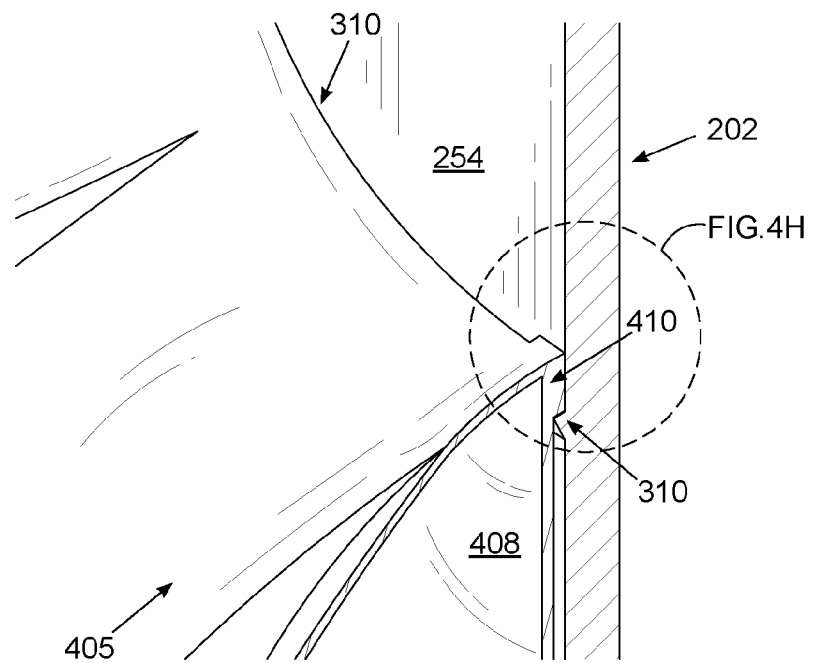
Figure 4H:
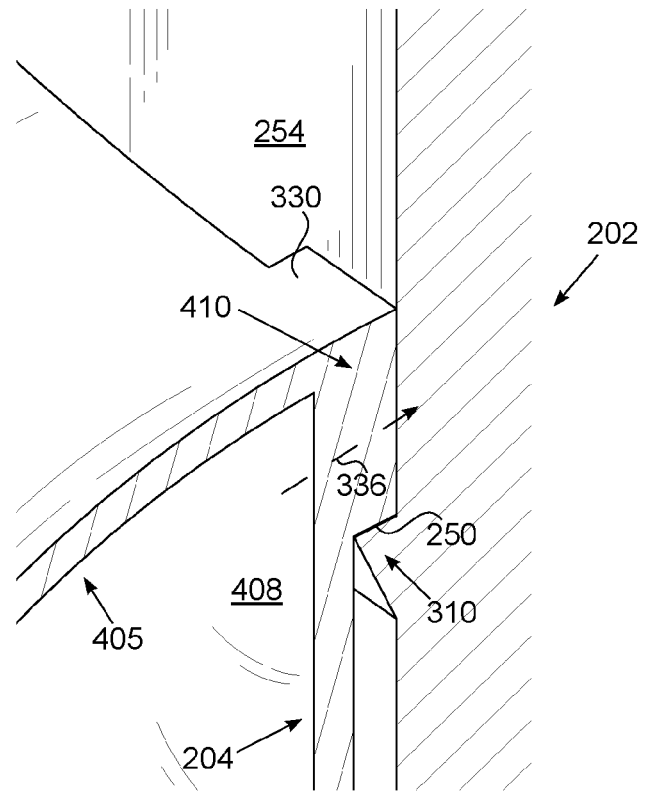
Figure 5A:
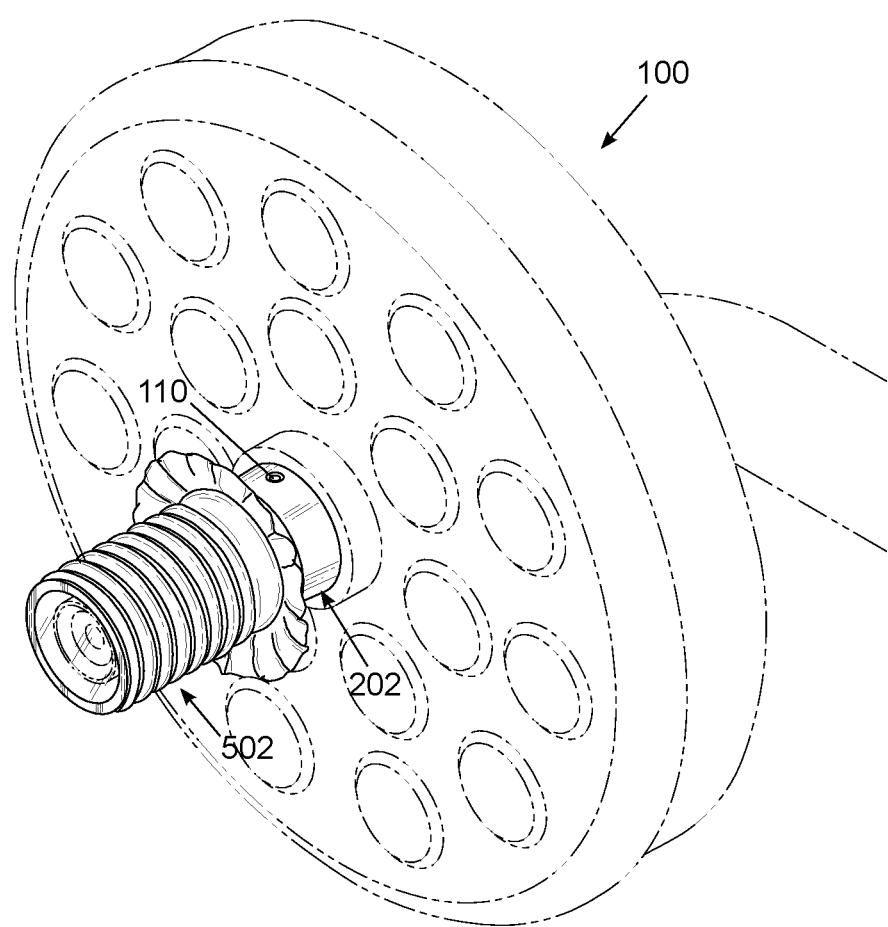
FIGS. 5A to 5D are non-limiting, exemplary illustrations of soft, pliable, disposable, universal replacement camera cover 502 in accordance with another embodiment of the present invention.
Figures 5B, 5C:
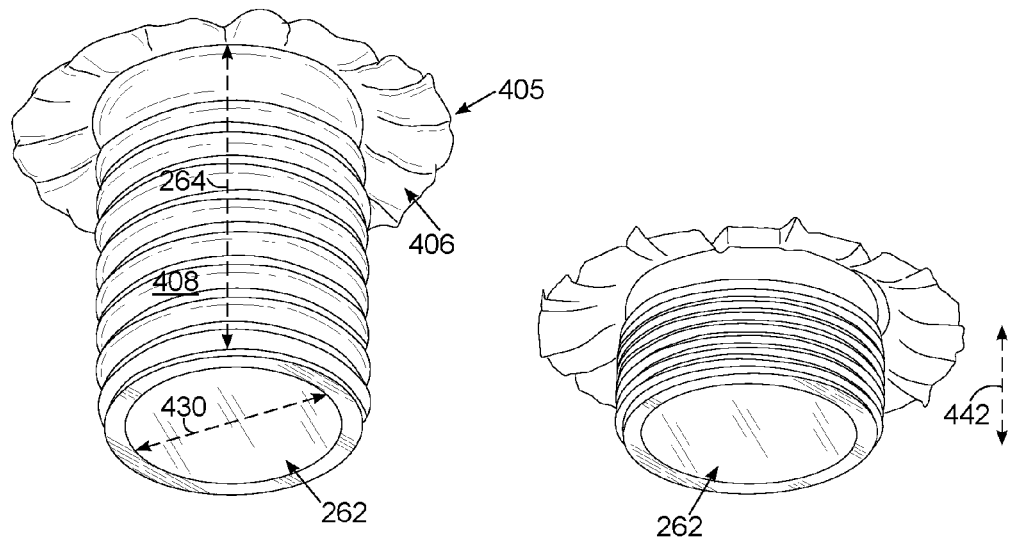
Figure 5D:
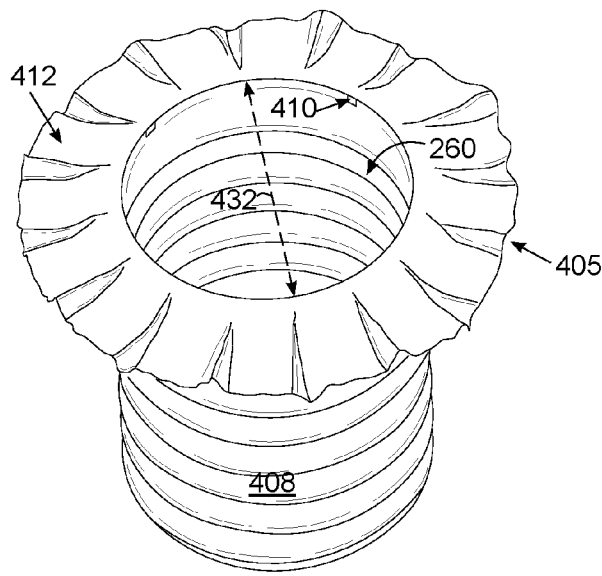

FIGS. 4E and 4F non-limiting, exemplary enlarged view illustrations that illustrate engagement members 410 of upper section 402 of soft, pliable, disposable universal (and sterilized) replacement camera cover 204 at edge 334 of ledge 250 of securing structure 310 of universal adapter interface unit 202. At this position, upper section 402 of soft, pliable, disposable universal (and sterilized) replacement camera cover 204 is stretched away (as shown by arrow 336) from surface 254 of universal adapter interface unit 202. FIGS. 4G and 4H are non-limiting, exemplary enlarged view illustrations that illustrate engagement members 410 of upper section 402 of soft, pliable, disposable universal (and sterilized) replacement camera cover 204 snapped back (as shown by arrow 336) onto surface 254 and secured on ledge 250 of securing structure 310 of universal adapter interface unit 202. The stretching action (FIGS. 4E and 4F) and the snap back action (FIGS. 4G and 4H) provides a "maker" or "index" coupling functionality that enables users to "feel" the correct mounting position of soft, pliable, disposable universal (and sterilized) replacement camera cover 204 as cover 204 is detachably mounted and secured onto universal adapter interface unit 202.

In general, soft, pliable, disposable universal (and sterilized) replacement camera cover 204 is comprised of one of polypropylene (preferred) or polyethylene. Medical grade thermoformed polypropylene type of thermoplastic is preferred because it provides sufficient stiffness (or firmness) to maintain form and be able to be connected to universal adapter interface unit 202 via engagement members 410 (e.g., tabs). Further, polypropylene can withstand well-known gamma sterilization processes, which are extensively used for sterilization of single-use medical products. Withstanding gamma sterilization means that soft, pliable, disposable universal (and sterilized) replacement camera cover 204 would not discolor, and would not become brittle. Prevention of discoloration is important because when the end product (soft, pliable, disposable universal (and sterilized) replacement camera cover 204) is collapsed for storage and or delivery, it might create creases with visible lines if the product is discolored (turns "yellow") due to gamma sterilization. Visible creases are not esthetically desirable because they provide a "used" look-and-feel for the product.

In general, uses of various medical grades of polypropylene are preferred. A medical grade material may be defined as materials that meet United States Food and Drug Administration (FDA) and or United States Pharmacopeia (USP) requirements. A non-limiting example of a well-known medical grade polypropylene material that may be used may include, for example, Random Copolymers Polypropylene (RACO PP).

Soft, pliable, disposable, universal replacement camera cover 204 may be manufactured using any one of the very well known thermoforming process or blow molding process. With the embodiment illustrated in FIGS. 1A to 4H, thermoforming process is preferred, which may include well known compression molding type, vacuum forming type, or pressure forming type.

In general, soft, pliable, disposable, universal replacement camera cover 204 may comprise of polypropylene that has a thickness range of about 0.012 inch to about 0.020 inches, preferably 0.015 to 0.020 inches. A minimum of 0.015 inch thickness is preferred because during thermoforming process, the sheet of polypropylene with 0.015 inch thickness used to manufacture cover 204 (without polycarbonate lens) must be stretch to form the desired height product resulting in a much thinner end product with a thickness which must be equal to or greater than 0.0020 inches (preferably, 0.0025). If the end product (manufactured cover 204) thickness (at near the polycarbonate lens) is less than 0.0020 inches, the product will be perceived as having "pin holes," providing the perception that it will rupture (tear). It should be noted that as the polypropylene sheet is drawn or stretched to its final configuration due to thermoforming process, the portion near the polycarbonate lens area becomes the most stretched out (and hence, thinnest) portion, which must still have a thickness greater than or equal to 0.0020 inches. In other words, the 0.0020 inch minimum final thickness is sufficiently thick material that would provide sufficient structural integrity in terms of strength against possible tear or rupture. It should be noted that a thickness of greater than 0.020 inch for the end product (manufacture cover 204) results in a less pliable material. Further, even if still pliable, when cover 204 is collapsed for storage and delivery, when extended for use, cover 204 will show creases (cracks, stretch marks, etc.) due to material thickness, which is not desired because the creases make the product look old or used, or damaged.

Upper section 302 of universal adapter interface unit 202 (in terms of its length 340 and its inner diameter 324) may be varied to enable the manufacture of a single universal size for cover 204 with the use of the least amount of polypropylene material to save costs for manufacture of cover 204 (as cover 204 is disposable). As detailed below, to determine diameter 432 of the single universal size of cover 204 with the least amount of polypropylene material usage, diameter 324 of upper section 302 of universal adapter interface unit 202 may be configured commensurate with a make/model of surgical light camera 102 with the largest diameter 122. This configuration will enable cover 204 to easily fit onto and cover over other make and model surgical light cameras 102 with smaller diameters 122. As further detailed below, as to the overall length 440 for the single universal size of cover 204 with the least amount of polypropylene material usage, the length 340 of upper section 302 of universal adapter interface unit 202 may be configured commensurate with a make/model of surgical light camera 102 with the shortest height 120.

In general, a single size soft, pliable, disposable, universal replacement camera cover 204 may be used universally with varying sizes (lengthwise) universal adapter interface unit 202 in accordance with one or more embodiments of the present invention. The single (shortest possible) universal size of cover 204 may be determined based on the use of shortest height universal adapter interface unit 202 that may be used with the most popular shortest height make and model of surgical light cameras 102. Once the shortest height of the universal adapter interface unit 202 is determined for the shortest height surgical light camera 102, a determination may be made with respect to the minimum length of cover 204 needed to cover over the shortest length surgical light camera 102 selected wherein lens cover 262 is preferably about ¼ inch away from camera lens. Finally, for different makes and models of surgical light cameras 102 (with varying heights), the height of universal adapter interface unit 202 is varied to compensate for any height differentials or discrepancies for the single universal size of cover 204 when used with different makes and models of surgical light cameras 102 that may have longer height. This way, the preferred ¼ inch distance between cover lens 262 and camera lens 106 remains constant regardless of makes and models of surgical light cameras 102 and its height in relation to the single universal size of cover 204. Therefore, since upper section 302 of universal adapter interface unit 202 already varies for different makes/models of cameras, this means that its height/diameter may also be varied to accommodate for the constant height/diameter cover for different height/diameter surgical light cameras 102.

FIGS. 5A to 5D are non-limiting, exemplary illustrations of soft, pliable, disposable, universal replacement camera cover 502 in accordance with another embodiment of the present invention. Soft, pliable, disposable, universal replacement camera cover 502 illustrated in FIGS. 5A to 5D includes similar corresponding or equivalent components, interconnections, functional, operational, and or cooperative relationships as soft, pliable, disposable, universal replacement camera cover 204 that is shown in FIGS. 1A to 4H, and described above. Therefore, for the sake of brevity, clarity, convenience, and to avoid duplication, the general description of FIGS. 5A to 5D will not repeat every corresponding or equivalent component, interconnections, functional, operational, and or cooperative relationships that has already been described above in relation to soft, pliable, disposable, universal replacement camera cover 204 that is shown in FIGS. 1A to 4H. As illustrated in FIGS. 5A to 5D, soft, pliable, disposable, universal replacement camera cover 502 has a fold structure (accordion-like) configuration that collapses into a small, compact form. The fold structure may be formed using the very well known blow molding processes.

Although the invention has been described in considerable detail in language specific to structural features and or method acts, it is to be understood that the invention defined in the appended claims is not necessarily limited to the specific features or acts described. Rather, the specific features and acts are disclosed as exemplary preferred forms of implementing the claimed invention. Stated otherwise, it is to be understood that the phraseology and terminology employed herein, as well as the abstract, are for the purpose of description and should not be regarded as limiting. Further, the specification is not confined to the disclosed embodiments. Therefore, while exemplary illustrative embodiments of the invention have been described, numerous variations and alternative embodiments will occur to those skilled in the art. Such variations and alternate embodiments are contemplated, and can be made without departing from the spirit and scope of the invention.

It should further be noted that throughout the entire disclosure, the labels such as left, right, front, back, top, bottom, forward, reverse, clockwise, counter clockwise, up, down, or other similar terms such as upper, lower, aft, fore, vertical, horizontal, oblique, proximal, distal, parallel, perpendicular, transverse, longitudinal, etc. have been used for convenience purposes only and are not intended to imply any particular fixed direction or orientation. Instead, they are used to reflect relative locations and/or directions/orientations between various portions of an object.

In addition, reference to "first," "second," "third," and etc. members throughout the disclosure (and in particular, claims) is not used to show a serial or numerical limitation but instead is used to distinguish or identify the various members of the group.

In addition, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of," "act of," "operation of," or "operational act of" in the claims herein is not intended to invoke the provisions of 35 U.S.C. 112, Paragraph 6.

What is claimed is:

1. A replacement cover assembly, comprising:
a universal adapter interface unit; and
a soft, pliable, disposable universal replacement camera cover;
the universal adapter interface unit includes:
a first section that is specifically configured to detachably couple with a particular structure; and
a second section that is configured to universally, detachably couple with the soft, pliable, disposable, universal replacement camera cover;
the second section of the universal adapter interface unit includes a securing structure;
the securing structure is an interlocking surface structure on the second section;
the interlocking surface structure is a circumferential, upwardly projecting flange, protruding at an angle θ from an outer surface of the second section.

2. The replacement cover assembly as set forth in claim 1, wherein:
the soft, pliable, disposable, universal replacement camera cover has a first, expanded height for use, and a second, collapsed height for storage in a small, compact package.

3. The replacement cover assembly as set forth in claim 1, wherein:
the soft, pliable, disposable, universal replacement camera cover includes a viewing area.

4. The replacement cover assembly as set forth in claim 3, wherein:
the viewing area of the soft, pliable, disposable, universal replacement camera cover includes a lens.

5. The replacement cover assembly as set forth in claim 1, wherein:
the soft, pliable, disposable, universal replacement camera cover is comprised of:
a lower section; and
an upper section.

6. The replacement cover assembly as set forth in claim 5, wherein:
the lower section includes a viewing section with a lens.

7. The replacement cover assembly as set forth in claim 5, wherein:
the lower section further includes a body that houses and provides protective covering.

8. The replacement cover assembly as set forth in claim 7, wherein:
the body is generally cylindrical, with sufficient height and diameter to enable insertion and full, protective coverage for the camera.

9. The replacement cover assembly as set forth in claim 1, wherein:
the soft, pliable, disposable, universal replacement camera cover includes a barrier flange with sufficient span to prevent and block unintentional access into a non-sterile field;
barrier flange includes a first side that is within a sterile field section and a second side that faces the non-sterile field section.

10. The replacement cover assembly as set forth in claim 5, wherein:
the upper section has a universal coupling section that when engages a second section of the universal adapter interface unit, provides an indication of engagement.

11. The replacement cover assembly as set forth in claim 10, wherein:
the universal coupling sections are a set of tabs that engage a securing structure of the universal adapter interface unit.

12. A replacement cover assembly, comprising:
a universal adapter interface unit that includes a coupling index; and
a soft, pliable, disposable, universal replacement camera cover that detachably interlocks with the universal adapter interface unit at the coupling index;
the soft, pliable, disposable, universal replacement camera cover includes a viewing area that has a lens comprised of one of polycarbonate, polypropylene, and polystyrene which is coupled with the soft, pliable, disposable, universal replacement camera cover by a double sided adhesive member.

13. The replacement cover assembly as set forth in claim 12, wherein:
the soft, pliable, disposable, universal replacement camera cover includes a barrier that limits a grip of a user to within a sterile field, with the barrier having stiffener structures to provide sufficient stiffness that facilitates to prevent from flexing during normal operation.

14. The replacement cover assembly as set forth in claim 12, wherein:
the soft, pliable, disposable, universal replacement camera cover is comprised of one of polypropylene and polyethylene.

15. The replacement cover assembly as set forth in claim 12, wherein:
the soft, pliable, disposable, universal replacement camera cover includes a fold structure form-factor.

16. The replacement cover assembly as set forth in claim 15, wherein:
the fold structure is formed using blow molding processes.

17. The replacement cover assembly as set forth in claim 12, wherein:
the soft, pliable, disposable, universal replacement camera cover is manufactured using one of a thermoforming process and blow molding process.

18. The replacement cover assembly as set forth in claim 12, wherein:
the soft, pliable, disposable, universal replacement camera cover is comprised of polypropylene that has a thickness range of about 0.012 inch to about 0.020 inches, preferably about 0.015 to about 0.020 inches.

19. The replacement cover assembly as set forth in claim 12, wherein:
the soft, pliable, disposable, universal replacement camera cover has a barrier in a form an annular disc flange that functions to guard and limit a grip of a user to within a sterile field.

20. The replacement cover assembly as set forth in claim 19, wherein:
barrier includes stiffeners.

21. The replacement cover assembly as set forth in claim 20, wherein:
barrier includes coupling sections in a form of a tab that engage a securing structure of the universal adapter interface unit, with the securing structure providing fixed connection point that functions as indexing feature that is indicative of a proper connection point of the soft, pliable, disposable, universal replacement camera cover with universal adapter interface unit.

22. The replacement cover assembly as set forth in claim 21, wherein:
the coupling sections have a thickness of about less than or equal to 0.100 inches.

23. The replacement cover assembly as set forth in claim 12, wherein:
the soft, pliable, disposable, universal replacement camera cover has a barrier in a form an annular disc flange that has a curved cross-sectional profile,
wherein: a first side of the barrier that falls within a sterile field is generally convex, and a second side of the barrier is generally concave.

* * * * *